(12) United States Patent
Yamauchi et al.

(10) Patent No.: US 11,784,319 B2
(45) Date of Patent: Oct. 10, 2023

(54) METHODS FOR PRODUCING ALPHA-KETO ACID AND PYRUVIC ACID

(71) Applicant: JAPAN SCIENCE AND TECHNOLOGY AGENCY, Saitama (JP)

(72) Inventors: Miho Yamauchi, Fukuoka (JP); Tatsuyoshi Morimoto, Fukuoka (JP)

(73) Assignee: JAPAN SCIENCE AND TECHNOLOGY AGENCY, Saitama (JP)

(*) Notice: Subject to any disclaimer, the term of this patent is extended or adjusted under 35 U.S.C. 154(b) by 125 days.

(21) Appl. No.: 16/978,306

(22) PCT Filed: Mar. 5, 2019

(86) PCT No.: PCT/JP2019/008691
§ 371 (c)(1),
(2) Date: Sep. 4, 2020

(87) PCT Pub. No.: WO2019/172273
PCT Pub. Date: Sep. 12, 2019

(65) Prior Publication Data
US 2021/0057758 A1    Feb. 25, 2021

Related U.S. Application Data

(60) Provisional application No. 62/638,311, filed on Mar. 5, 2018.

(51) Int. Cl.
*H01M 4/90* (2006.01)
*C25B 5/00* (2006.01)
(Continued)

(52) U.S. Cl.
CPC ............ *H01M 4/9016* (2013.01); *C25B 5/00* (2013.01); *H01M 4/8882* (2013.01);
(Continued)

(58) Field of Classification Search
None
See application file for complete search history.

(56) References Cited

U.S. PATENT DOCUMENTS

2004/0126631 A1    7/2004   Uchida et al.
2006/0199047 A1    9/2006   Hojo et al.
(Continued)

FOREIGN PATENT DOCUMENTS

CN    1501537 A    6/2004
CN    1748332 A    3/2006
(Continued)

OTHER PUBLICATIONS

Office Action issued by the Indian Patent Office for Application No. 202027042840, dated Sep. 2, 2021, India.
(Continued)

*Primary Examiner* — Jonathan Crepeau
(74) *Attorney, Agent, or Firm* — Tim Tingkang Xia, Esq.; Locke Lord LLP

(57) ABSTRACT

This electrode catalyst of the present invention contains an electrically conductive material that supports a metal or a metal oxide, wherein electrical conductivity at 30° C. is $1 \times 10^{-13}$ Scm$^{-1}$ or greater.

2 Claims, 18 Drawing Sheets

(51) Int. Cl.
  *H01M 8/1011* (2016.01)
  *C07C 59/19* (2006.01)
  *C07C 51/16* (2006.01)
  *H01M 4/88* (2006.01)
  *H01M 4/92* (2006.01)
(52) U.S. Cl.
  CPC ......... *H01M 4/9041* (2013.01); *H01M 4/921* (2013.01); *H01M 4/926* (2013.01); *H01M 8/1013* (2013.01); *C07C 51/16* (2013.01); *C07C 59/19* (2013.01)

(56) References Cited

U.S. PATENT DOCUMENTS

| | | | | |
|---|---|---|---|---|
| 2007/0131546 A1* | 6/2007 | Nomoto | ............ | H01M 8/16 204/403.01 |
| 2013/0065090 A1 | 3/2013 | Kazuno et al. | | |
| 2018/0047993 A1 | 2/2018 | Inaba et al. | | |
| 2019/0134609 A1 | 5/2019 | Yamauchi et al. | | |

FOREIGN PATENT DOCUMENTS

| | | | |
|---|---|---|---|
| CN | 101395747 | A | 3/2009 |
| CN | 103402633 | A | 11/2013 |
| CN | 105481678 | * | 4/2016 |
| CN | 107887618 | A | 4/2018 |
| JP | 10162839 | A | 6/1998 |
| JP | 11273690 | | 10/1999 |
| JP | 2003146935 | * | 5/2003 |
| JP | 2004134132 | A | 4/2004 |
| JP | 2006092957 | A | 4/2006 |
| JP | 2006202701 | A | 8/2006 |
| JP | 2013151392 | A | 8/2013 |
| JP | 2017029967 | A | 2/2017 |
| JP | 2018060716 | A | 4/2018 |
| JP | 2009523066 | A | 6/2019 |
| WO | 2004070865 | A1 | 8/2004 |
| WO | 2017154743 | A1 | 9/2017 |

OTHER PUBLICATIONS

Office Action issued by the China Patent Office for Chinese Application No. 201980029758.9, dated Dec. 3, 2021, China.
Japan Patent Office, "International Search Report for PCT Application No. PCT/JP2019/008691", Japan, dated Jun. 4, 2019.
Wang, Wenming et al., "One-step synthesis of carbon-supported Pd—Pt alloy electrocatalysts for methanol tolerant oxygen reduction", Electrochemistry Communications, 2008, vol. 10, pp. 1396-1399.
Li, Huanqiao et al., "Design and Preparation of Highly Active Pt—Pd/C Catalyst for the Oxygen Reduction Reaction", J. Phys. Chem. C, 2007; vol. 111, No. 15, pp. 5605-5617.
Daimon, Hideo et al., "Developmet of Highly Active and Durable Pt—Pd System Catalysts for PEFCs", Proceedings of the 23rd ECDIC Fuel Cell Symposium, May 26, 2016, pp. 254-255.
Okuno et al., ORR activity and microstrucutre of PtPd/C alloy catalyst for PEFC,Lecture abstracts of the 55th Battery Symposium in Japan, Nov. 19, 2014, p. 609.
Office Action issued by the China Patent Office for Chinese Application No. 201980029758.9, dated Aug. 3, 2022,China.
Zafer Ozturk, et al., "The preparation and characterization of nano-sized Pt—Pd/C catalysts and comparison of their superior catalytic activities for methanol and ethanol oxidation", J Mater Sci (2012) 47: 8134-8144.
Jin-Yeon Lee, et al., "Synthesis of cubic PtPd alloy nanoparticles as anode electrocatalysts for methanol and formic acid oxidation reactions", Phys. Chem. Chem. Phys., 2015, 17, 8642-8648.
Office Action issued by the Japan Patent Office for Application No. 2020-505058, dated Feb. 7, 2023, Japan.
Office Action issued by the State Intellectual Property Office of the Peoples Republic of China for Application No. 201980029758.9, dated Mar. 3, 2023, China.
Office Action issued by the Japan Intellectual Property Office for Application No. 2020-505058, dated Aug. 22, 2023, Japan.

* cited by examiner

METHODS FOR PRODUCING ALPHA-KETO ACID AND PYRUVIC ACID

CROSS-REFERENCE TO RELATED PATENT APPLICATION

This application claims priority to U.S. Provisional Application No. 62/638,311, filed Mar. 5, 2018, the whole content of which is incorporated herein by reference.

TECHNICAL FIELD

The present invention relates to an electrode catalyst, a method for producing a carrier-supported metal alloy, a method for electrochemically producing ketones using an electrode catalyst, a method for producing hydroxycarboxylic acids such as pyruvic acid, and a fuel cell.

BACKGROUND OF THE INVENTION

Efficient use of biomass resources composed of carbon derived from carbon dioxide in the atmosphere is considered to be an effective way of reducing consumption of petroleum resources. In recent years, the production of bioalcohols such as ethanol and ethylene glycol which are used as fuels and raw materials has been industrialized. In the current industrial process, bioethanol is produced by alcoholic fermentation with enzymes using sugar or the like as a raw material, but this process has a problem of low carbon yield. On the other hand, a method of producing an alcohol by hydrogenation from a carboxylic acid abundantly contained in biomass has been attracting attention (for example, refer to Patent Document 1). Further, if energy can be extracted from the alcohol produced from the biomass as a raw material, a carbon neutral cycle can be realized using alcohol as an energy carrier.

Much research has been conducted on techniques regarding fuel cells for converting alcohols into carboxylic acids. In particular, Pt—Pd based catalysts have been attracting attention as electrode catalysts.

As a methanol oxidation catalyst, an alloy obtained by adding Pd to Pt has been known. A rule of thumb known as Vegard's Law has been known as an index for the structures of alloys. The rule of thumb is that the lattice constant of an alloy is an arithmetic mean of the lattice constants of component metals. For example, the lattice constant of $Pt_xPd_{100-x}$, $a(Pt_{100-a}Pd_n, 0<n<100)$, can be expressed by the following formula (1).

$$a(Pt_{(100-a)}Pd_n) = a(Pt) \times ((100-n)/100) + a(Pd) \times (n/100) \quad (1)$$

A method for producing Pt—Pd/C nanoparticles by a polyol method using ethylene glycol as a solvent and a reducing agent has been known (for example, refer to Non-Patent Document 1). In this production method, trisodium citrate serving as a complexing agent and a stabilizing agent, electrically conductive carbon black serving as a carrier, and palladium acetylacetonate [Pd(acac)$_2$] and platinum acetylacetonate [Pt(acac)$_2$] were dissolved in ethylene glycol which was also a reducing agent, and the resulting mixture was heated to reflux at 175° C. for 6 hours to carry out a reduction reaction. After the completion of the reaction, the product is cooled to room temperature and then washed, and dried at 75° C. for 12 hours to produce a sample. Pt—Pd in the obtained sample is in the form of nanoparticles having a diameter of about 4.7 nm to 5.2 nm. The nanoparticles have larger lattice constants obtained from the powder XRD pattern than those estimated from Vegard's law.

Further, a method for producing $Pt_3Pd_1/C$ and $Pt_1Pd_1/C$ using a carbon suspension obtained by suspending carbon black pretreated with 1M hydrochloric acid and 2M nitric acid in ethylene glycol has been known (for example, refer to Non-Patent Document 2). In this production method, carbon black pretreated with aqua regia is suspended in ethylene glycol to prepare a carbon suspension. While performing ultrasonic treatment, an aqueous solution obtained by dissolving $H_2PtCl_6 \cdot 6H_2O$ and $PdCl_2$ is added dropwise to the carbon suspension, and the mixed solution of the carbon suspension and the above aqueous solution is stirred. Then, an aqueous NaOH solution is added to the above mixed solution to adjust the pH of the mixed solution to 12 to 13. The pH-adjusted mixed solution is heated at 130° C. for 3 hours to reduce metal ions, thereby obtaining $Pt_3Pd_1/C$ and $Pt_1Pd_1/C$. The obtained $Pt_3Pd_1/C$ and $Pt_1Pd_1/C$ are washed with distilled water and dried under reduced pressure at 70° C. for 8 hours when chloride ions are no longer detected in the $AgNO_3$ solution (1 mol/L). The average primary particle size of $Pt_3Pd_1/C$ obtained from a low resolution transmission electron microscope (TEM) image is 2.8 nm, and the average primary particle size of $Pt_1Pd_1/C$ is 3.6 nm. The lattice constant obtained from the powder XRD pattern of $Pt_3Pd_1/C$ is $3.916 \times 10^{-10}$ m, and the lattice constant obtained from the powder XRD pattern of $Pt_1Pd_1/C$ is $3.910 \times 10^{-10}$ m. As described above, the lattice constant obtained from the $Pt_3Pd_1/C$ powder XRD pattern and the lattice constant obtained from the $Pt_1Pd_1/C$ powder XRD pattern are larger than the lattice constants estimated from Vegard's law.

CITATION LIST

Patent Document 1: International Patent Publication No. 2017/154743
Non-Patent Document 1: W. Wang et al., Electrochemistry Communications, 10, 1396-1399 (2008)
Non-Patent Document 2: H. Li et al., J. Phys. Chem. C, 111, 5605-5617 (2007)

SUMMARY OF THE INVENTION

Technical Problem

The present invention has been made in view of the above circumstances, with an object of providing an electrode catalyst having excellent catalytic activity as an alcohol oxidation catalyst or a lactic acid oxidation catalyst, a fuel cell including an electrode provided with the aforementioned electrode catalyst, a method for producing ketones using the aforementioned electrode catalyst, a method for producing pyruvic acid using the aforementioned electrode catalyst, and a method for producing a carrier-supported metal alloy.

Solution to Problem

The inventors of the present invention have found that: since metal elements are uniformly mixed and reacted and the electron transfer between Pd atoms and Pt atoms occurs easily, an ideal surface structure and electronic state for activating alcohols are established in the Pt—Pd/C nanoparticles having a lattice constant estimated from the Vegard's law as described above, thereby, as an alcohol oxidation catalyst, allowing an oxidation reaction to proceed highly selectively; and also that: the reaction starts at low voltage, to complete the present invention.

(1) An electrode catalyst including an electrically conductive material carrying a metal or a metal oxide, and having an electrical conductivity at 30° C. of $1\times10^{-13}$ Scm$^{-1}$ or more.

(2) The electrode catalyst according to (1), wherein the aforementioned metal is a transition metal and the aforementioned metal oxide is a transition metal oxide.

(3) The electrode catalyst according to (1) or (2), wherein the aforementioned metal includes any one metal or two or more alloys selected from the group consisting of Pd, Pt, Au, Jr, Ru, Rh, and Ag.

(4) The electrode catalyst according to any one of (1) to (3), including any one metal selected from the group consisting of Pd, Pt, Ru, and Ir or an alloy containing two or more metals, and having an electrical conductivity at 30° C. of $1\times10^{-13}$ Scm$^{-1}$ or more.

(5) The electrode catalyst according to (3) or (4), wherein the aforementioned Pd and Pt are in a solid solution state.

(6) The electrode catalyst according to (4), wherein the aforementioned alloy follows Vegard's law.

(7) The electrode catalyst according to (3) to (6), wherein an alloy including the aforementioned Pt and Pd have a Pt content of 50 atomic % or more of the alloy.

(8) The electrode catalyst according to (3) to (7), wherein the aforementioned alloy has a work function smaller than an arithmetic mean of work functions of the metals.

(9) The electrode catalyst according to any one of (1) to (8), wherein the aforementioned metal is in a form of a particle having a diameter of 500 nm or less.

(10) The electrode catalyst according to (9), wherein the aforementioned metal is in a form of a particle having a diameter of 10 nm or less.

(11) A method for producing ketones and carboxylic acids, the method including a step of using an alcohol as a raw material and using a catalyst to carry out an electrochemical oxidation reaction of the aforementioned alcohol.

(12) A method for producing ketones and carboxylic acids, wherein the aforementioned catalyst is the electrode catalyst according to (1) to (10).

(13) The method for producing ketones and carboxylic acids according to (11) or (12), wherein the aforementioned alcohol is a secondary alcohol.

(14) The method for producing ketones and carboxylic acids according to (13), wherein the aforementioned secondary alcohol contains a carboxyl group.

(15) The method for producing ketones and carboxylic acids according to (11) to (14), wherein the aforementioned alcohol is a secondary alcohol, and the secondary alcohol is a hydroxycarboxylic acid that is a substituent at an α-position of a carboxyl group.

(16) The method for producing ketones and carboxylic acids according to (15), wherein the aforementioned hydroxycarboxylic acid is lactic acid or pyruvic acid.

(17) The method for producing ketones and carboxylic acids according to (11) or (12), wherein the aforementioned alcohol is a primary alcohol.

(18) The method for producing ketones and carboxylic acids according to (17), wherein the aforementioned primary alcohol is a hydroxycarboxylic acid that is a substituent at an α-position of a carboxyl group.

(19) The method for producing ketones and carboxylic acids according to (18), wherein the aforementioned hydroxycarboxylic acid is glycolic acid.

(20) A method for producing a carrier-supported metal alloy, including:

(a) a step of dissolving one or two metal reagents in a solvent;

(b) a step of bringing an electrically conductive material into contact;

(c) a step of reacting the aforementioned metal reagent with the aforementioned electrically conductive material, and then reducing a product obtained by the reaction with a metal hydride reagent; and (d) a step of treating the product reduced by the aforementioned metal hydride reagent at 20° C. to 500° C. in the presence of hydrogen.

(21) The method for producing a carrier-supported metal alloy according to (20), wherein the aforementioned metal reagent is a Pd reagent, a Pt reagent, and an Ir reagent.

(22) The method for producing a carrier-supported metal alloy according to (20) or (21), wherein the aforementioned electrically conductive material is activated carbon or a transition metal.

(23) The method for producing a carrier-supported metal alloy according to any one of (20) to (22), wherein the aforementioned metal hydride reagent is NaBH$_4$.

(24) A fuel cell including an anode, a cathode and an electrolyte, the fuel cell that includes an electrode catalyst on a surface or inside of the anode, or on the electrolyte side of the anode, and directly generates electricity when alcohols are brought into contact with the aforementioned catalyst and electrochemically oxidized to produce ketones or carboxylic acids.

(25) The fuel cell according to (24), wherein the aforementioned electrode catalyst is the electrode catalyst according to (1) to (10).

(26) The fuel cell according to (24) or (25), wherein an alcohol is brought into contact with the aforementioned electrode catalyst and oxidized to produce a carboxylic acid in the aforementioned anode.

(27) An energy recovery system for recovering surplus electric power energy, the system including: (a) a container for storing carboxylic acids; (b) a means for reducing carboxylic acids to alcohols using surplus electric power; (c) a means for storing the obtained alcohols; and (d) a means for oxidizing the aforementioned alcohols to produce the aforementioned carboxylic acids and generating electric power.

Advantageous Effects of the Invention

According to the present invention, it is possible to provide an electrode catalyst having excellent catalytic activity as an alcohol oxidation catalyst or a lactic acid oxidation catalyst, a fuel cell including an electrode provided with the aforementioned electrode catalyst, a method for producing ketones using the aforementioned electrode catalyst, a method for producing pyruvic acid using the aforementioned electrode catalyst, and a method for producing a carrier-supported metal alloy. Further, according to the present invention, a cycle of producing an alcohol from a carboxylic acid and producing a carboxylic acid from an alcohol becomes possible. Furthermore, according to the present invention, an alloy following Vegard's law can be obtained.

DESCRIPTION OF EMBODIMENTS

Figure 1:
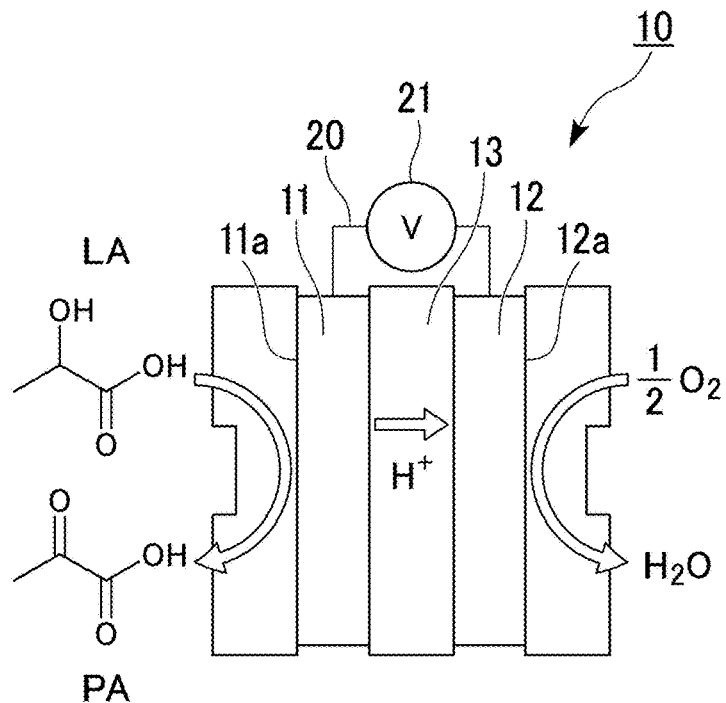
FIG. 1 is a schematic diagram showing a schematic configuration of a fuel cell according to the present invention.

Embodiments of the electrode catalyst, the fuel cell, the method for producing ketones, the method for producing pyruvic acid, and the method for producing a carrier-supported metal alloy of the present invention will be described.

It should be noted that the present embodiment is specifically described for better understanding of the scope and gist of the invention, and does not limit the present invention unless otherwise specified.

Electrode Catalyst

An electrode catalyst of the present embodiment contains an electrically conductive material carrying a metal or a metal oxide, and has an electrical conductivity at 30° C. of $1×10^{-13}$ $Scm^{-1}$ or more.

The electrical conductivity of the electrode catalyst of the present embodiment at 30° C. is $1×10^{-13}$ $Scm^{-1}$ or more, and preferably 1 $Scm^{-1}$ or more. The upper limit of the electrical conductivity may be $7×10^7$ $Scm^{-1}$ or less, or may be $6×10^2$ $Scm^{-1}$ or less.

If the electrical conductivity at 30° C. is less than $1×10^{-13}$ $Scm^{-1}$, the electrons flowing from the circuit do not reach substrate molecules and the reaction does not start.

As the method for measuring the electrical conductivity of the catalyst, an AC impedance method and the like can be mentioned.

Examples of the metal include transition metals and typical metal elements, and transition metals are preferable from the viewpoint of forming a chemical bond having a strength suitable for reaction with a substrate molecule.

Examples of the metal oxide include transition metal oxides and metal oxides of typical elements, and transition metal oxides are preferable from the viewpoints of efficiency of the reaction activation and chemical stability.

Examples of the transition metal include scandium (Sc), titanium (Ti), vanadium (V), chromium (Cr), manganese (Mn), iron (Fe), cobalt (Co), nickel (Ni), copper (Cu), yttrium (Y), zirconium (Zr), niobium (Nb), molybdenum (Mo), technetium (Tc), ruthenium (Ru), rhodium (Rh), palladium (Pd), silver (Ag), lanthanum (La), cerium (Ce), praseodymium (Pr), neodymium (Nd), promethium (Pm), samarium (Sm), europium (Eu), gadolinium (Gd), terpium (Tb), dysprosium (Dy), holmium (Ho), erbium (Er), thulium (Tm), ytterbium (Yb), lutetium (Lu), hafnium (Hf), tantalum (Ta), tungsten (W), rhenium (Re), osmium (Os), iridium (Ir), platinum (Pt) and gold (Au).

Examples of the transition metal oxide include oxides of the above transition metals.

Examples of the typical metal element include lithium (Li), sodium (Na), potassium (K), rubidium (Rb), cesium (Cs), francium (Fr), beryllium (Be), magnesium (Mg), calcium (Ca), strontium (Sr), barium (Ba), radium (Ra), zinc (Zn), cadmium (Cd), mercury (Hg), copernicium (Cn), aluminum (Al), gallium (Ga), indium (In), thallium (Tl), ununtrium (Unt), germanium (Ge), tin (Sn), lead (Pb), freropium (Fl), antimony (Sb), bismuth (Bi), ununpentium (Unp), polonium (Po) and livermolium (Lv).

Examples of the metal oxides of typical elements include oxides of the above typical metal elements.

The electrically conductive material used in the electrode catalyst of the present embodiment is a carrier for the catalyst and has an important function as an electrode because it is responsible for electrical conductivity. Examples of such electrically conductive materials include activated carbon and transition metals.

The electrode catalyst of the present embodiment preferably contains any one or two or more types of metals selected from the group consisting of Pd, Pt, Au, Ir, Ru, Rh, and Ag. It should be noted that the electrode catalyst of the present embodiment may contain an oxide of the above metals.

By containing any one or two or more types of metals selected from the group consisting of Pd, Pt, Au, Ir, Ru, Rh, and Ag, the catalytic activity is improved in the production of a ketone or pyruvic acid, as compared with the case of containing other metals.

The electrode catalyst of the present embodiment preferably contains an alloy containing any one or two or more types selected from the group consisting of Pd, Pt, Ru and Ir. It should be noted that in the electrode catalyst of the present embodiment, the above alloy may include an oxide of the above metal.

When the electrode catalyst contains an alloy containing any one or two or more types selected from the group consisting of Pd, Pt, Ru, and Ir, the catalytic activity is improved in the production of a ketone or pyruvic acid, as compared with the case of containing other metals.

The electrode catalyst of the present embodiment preferably has an electrical conductivity at 30° C. of $1 \times 10^{-13}$ Scm$^{-1}$ or more when containing an alloy containing any one or two or more types selected from the group consisting of Pd, Pt, Ru, and Ir. Further, it is preferable that the alloy described above follows the Vegard's law. That is, it is preferable that in the alloy constituting the electrode catalyst of the present embodiment, there is an approximately proportional relationship between the lattice constant of the alloy and the concentration of the compositional element. For example, when the alloy is composed of Pd and Pt, the alloy is represented by the general formula $Pt_xPd_{100-x}$ ($0<x<100$). The lattice constant of $Pt_xPd_{100-x}$, $a(Pt_{(100-n)}Pd_n)$, $0<n<100$), can be expressed by the following formula (1).

$$a(Pt_{(100-n)}Pd_n) = a(Pt) \times ((100-n)/100) + a(Pd) \times (n/100) \quad (1)$$

If the alloy constituting the electrode catalyst of the present embodiment follows the Vegard's law, it is more excellent in catalytic activity in the production of a ketone or pyruvic acid than in the case of not following the Vegard's law. Furthermore, when the alloy follows Vegard's law, in terms of the work function of the alloy, it is preferable that the alloy exhibits a work function smaller than the arithmetic mean of the work functions of the component metals constituting the alloy.

A method to examine that the electrode catalyst follows Vegard's law is as follows.

An accurate lattice constant of the alloy can be obtained by analysis using the Rietveld method by measuring a powder X-ray diffraction pattern of an electrode catalyst with a high signal noise (S/N) ratio using radiated light having a strong line intensity. Although a diffraction pattern can be obtained using a commercially available device equipped with a tube, a lattice constant may not be obtained in some cases because a pattern with a low S/N ratio is obtained. In addition, the lattice constant can be obtained by analyzing single or multiple diffraction peaks using the Le Bail method, but the accuracy may be lacking in some cases.

In the present embodiment, the catalyst performs an electrochemical oxidation reaction, but since the present embodiment uses surplus electric power, it is required to start the reaction at a potential as low as possible. For that purpose, at this time, electrons need to be provided to the oxidation reaction from a catalytic metal to which an electrical potential is applied. The easiness of provision thereof depends on the relationship between the work function of the alloy and the reactivity of the reaction substrate, but in the study of the present embodiment, the catalytic reaction can be started at an even lower potential by the catalyst becoming a solid solution. In the case of Pt and Pd, the ratio of this type of alloy is preferably such that the alloy composed of Pt and Pd has a Pt content of 50 atomic % or more of the alloy. In the case of such a ratio, the reaction can be started at an even lower potential. Furthermore, at that time, a feature was found in that the work function of the alloy was lower than the arithmetic mean of those of both component elements.

Although several methods for obtaining the work function are known, since the alloy on the catalyst carrier is in the form of nanoparticles, a high-resolution method is necessary for the measurement. In the present embodiment, the measurement was performed using ultraviolet photoelectron spectroscopy (UPS). The principle of photoelectron spectroscopy is the same as that of XPS. Ultraviolet rays used in UPS have lower energy and narrower energy width than those used in XPS. Therefore, the surface state can be examined with higher resolution than XPS. In addition, UPS can measure work function (q) which is energy required for extracting an electron from a material.

For metals and semiconductors, the work function is obtained by the following equation using the energy hv of the irradiation light and the energy width W of the UPS spectrum.

$$\varphi = h\nu - W$$

hv is the energy of the irradiated ultraviolet ray, which is 21.1 eV for the HeI line. Further, the energy width W of the UPS spectrum is obtained from the energy at the rising position of the valence band and the energy at the rising position on the high binding energy side. The energy at the rising position of the valence band and the energy at the rising position on the high binding energy side can be obtained by extrapolating the UPS spectrum with a straight line and determining an intersection with the background.

The method for measuring the contents of Pd and Pt in the electrode catalyst is as follows.

They can be examined by measurement by an inductively coupled plasma method such as ICP-AES or ICP-MS, or energy dispersive X-ray analysis (EDS) measurement combined with a scanning transmission electron microscope (STEM).

When the electrode catalyst of the present embodiment contains Pd and Pt or is an alloy containing Pd and Pt, it is preferable that Pd and Pt are in solid solution states.

When Pd and Pt are in solid solution states, a surface structure advantageous for activating the substrate molecule and a favorable electronic state for promoting alcohol oxidation due to electron transfer between Pd and Pt are formed.

The method for confirming that Pd and Pt are in solid solution states is as follows.

By the element distribution measurement using a scanning transmission electron microscope (STEM) and an energy dispersive X-ray analyzer (EDS), it is possible to roughly observe the mixed state of constituent elements. Furthermore, confirmation as a sufficiently mixed solid solution is possible if it is confirmed that the lattice constant obtained from the powder XRD diffraction satisfies Vegard's law.

The electrode catalyst of the present embodiment may include, as an electrode carrier, an electrically conductive material for supplying electricity from an external circuit to the electrode catalyst, in addition to the above metals and metal oxides. Examples of the electrically conductive material include metals, oxides and carbon materials. Carbon (C) may be contained as a general and inexpensive electrically conductive material. When the electrode catalyst of the present embodiment contains carbon (C), for example, a carbon-supported platinum-palladium alloy nanoparticle catalyst represented by the general formula $Pt_xPd_{100-x}/C$ (0<x<100) is preferable.

The shape of the electrode catalyst of the present embodiment may be any shape such as a spherical shape, needle-like shape and plate shape, but it is desirable that the specific surface area of the electrode catalyst is large from the viewpoint of maximizing the number of active sites. The size of a particle is defined as the longest diameter of the cut surface when the particle is cut.

The electrode catalyst of the present embodiment is preferably particles having a diameter of 500 nm or less, more preferably particles having a diameter of 50 nm or less, and still more preferably particles having a diameter of 5 nm or less. The electrode catalyst of the present embodiment may be particles having a diameter of 0.5 nm or more, and preferably may be particles having a diameter of 1.5 nm or more.

When the electrode catalyst is particles having a diameter of 50 nm or less, since the specific surface area of the catalyst becomes large, the contact area between the electrode catalyst and the target material becomes large, and the catalytic activity improves. Further, when the electrode catalyst is particles having a diameter of 5 nm or less, more preferably 5 nm or less, since the specific surface area of the electrode catalyst becomes larger, the contact area between the electrode catalyst and the target material becomes larger, and the catalytic activity further improves.

The diameter of the electrode catalyst of the present embodiment can be calculated by measuring the diameters of the catalyst particles in a TEM image measured using a transmission electron microscope and subjecting them to statistical processing.

The electrode catalyst of the present embodiment is composed of a metal or a metal oxide and has an electrical conductivity of $1 \times 10^{-13}$ Scm$^{-1}$ at 30° C. or more, and therefore has an excellent catalytic activity as an alcohol oxidation catalyst or a lactic acid oxidation catalyst.

Method for Producing Carrier-Supported Metal Alloy

The electrode catalyst of the present invention can be produced by the following method. That is, a method for producing a carrier-supported metal alloy, including:

(a) a step of dissolving one or two metal reagents in a solvent;

(b) a step of bringing an electrically conductive material into contact;

(c) a step of reacting the aforementioned metal reagent with the aforementioned electrically conductive material, and then reducing a product obtained by the reaction with a metal hydride reagent; and (d) a step of treating a compound of the above step (b) at 20° C. to 500° C. in the presence of hydrogen.

The metal reagent preferably contains any one or two or more types selected from the group consisting of a Pd reagent, a Pt reagent, a Ru reagent and an Ir reagent. These reagents are preferably reagents that are uniformly soluble in a reaction liquid such as water or an organic solvent.

When the metal reagent contains any one or two or more types selected from the group consisting of a Pd reagent, a Pt reagent, a Ru reagent and an Ir reagent, it is possible to oxidize substrate molecules more efficiently than the case of containing other reagents.

The electrically conductive material may be introduced as a precursor or may be used as carrier particles. More specifically, activated carbon and transition metals are preferable.

By using activated carbon or a transition metal as the electrically conductive material, electrons generated by an oxidation reaction on the catalyst can be efficiently circulated to the external circuit.

In the present invention, the above metal reagent, carrier or carrier precursor is added to water or an organic solvent to react in a uniform state.

As a metal ion reducing agent, it is appropriate to use a compound having a standard reduction potential that is more negative than that of hydrogen (0 eV) at room temperature, from the viewpoint of its strong capacity to reduce transition metal ions to metals. Examples of such reducing agents include $MBH_4$, $MEt_3BH$ (M=Na, K), sodium cyanoborohydride ($NaBH_3CN$), lithium borohydride ($LiBH_4$), lithium triethylborohydride ($LiBHEt_3$), borane complexes ($BH_3.L$), triethylsilane ($Et_3SiH$) and sodium bis(2-methoxyethoxy) aluminum hydride (Red-Al). However, it requires careful attention because some of these reducing agents cannot be used in an aqueous solution, as they explosively react with water and are therefore dangerous. In that case, it is appropriate to use a solvent other than water (for example, an aprotic polar solvent such as tetrahydrofuran, N,N-dimethylformamide and dimethyl sulfoxide) as the solvent. Of these, NaBH$_4$ is preferable as the reducing agent because it is water-soluble and easy to handle.

The resultant is further subjected to a reduction treatment at high temperature in hydrogen gas. The treatment is usually carried out at a temperature of 20° C. to 500° C., and preferably 80° C. to 250° C. It is preferable to carry out the treatment within this temperature range from the viewpoints of sufficiently performing the reduction treatment and satisfactorily transforming the component metals into solid solutions. Further, the treatment time is usually from 0.1 to 12 hours, and preferably from 1 to 3 hours. Performing the reduction treatment within this time range is preferable in that the reduction treatment can be sufficiently performed in a short period of time. Further, the reaction is carried out under hydrogen flow, and 99.99% industrial hydrogen gas is used as hydrogen gas. Industrial hydrogen gas is preferable because it can sufficiently reduce the metal.

A method for producing the electrode catalyst of the present embodiment will be described.

Here, as an example of the method for producing the electrode catalyst of the present embodiment, a method for producing the carbon-supported platinum-palladium alloy nanoparticle catalyst represented by the general formula Pt$_x$Pd$_{100-x}$/C (0<x<100) will be described.

A predetermined amount of 2-ethoxyethanol, hexachloroplatinic (IV) acid (H$_2$PtCl$_6$) aqueous solution, palladium (II) acetate (Pd(OAc)$_2$) and acetone were introduced into a test tube, and H$_2$PtCl$_6$ and Pd(OAc)$_2$ are dissolved in the solution by ultrasonication.

Next, a predetermined amount of carbon black is added to the obtained solution, and the contents are thoroughly mixed by ultrasonication.

Then, the mixture is stirred while bubbling argon or nitrogen (N$_2$) gas.

After a predetermined time has passed, the argon or nitrogen (N$_2$) bubbling is changed to flowing, and a solution obtained by dissolving sodium borohydride in water is added dropwise little by little with a Pasteur pipette. At this time, the liquid temperature is kept constant.

In order to allow the reaction to proceed sufficiently, the temperature is raised to a predetermined temperature and kept at that temperature for a predetermined time.

Then, the resultant is allowed to cool.

The product is separated from the solution by washing the product from the test tube into a centrifuge tube with acetone and centrifuging for a predetermined time.

Furthermore, an operation of adding acetone and centrifuging for a predetermined time is repeated twice.

Then, an operation of adding acetone and water and centrifuging for a predetermined time is repeated twice.

Thereafter, acetone is added, and the product is washed into a flask by ultrasonication, subjected to suction filtration using a membrane filter, washed with water and acetone, and vacuum dried for a predetermined time using a desiccator.

After drying, a carbon-supported platinum-palladium alloy nanoparticle catalyst represented by the general formula Pt$_x$Pd$_{100-x}$/C (0<x<100) is obtained.

Fuel Cell

A fuel cell of the present embodiment includes the electrode catalyst of the present embodiment on the surface or inside of an anode, or on the electrolyte side of the anode. Further, the fuel cell of the present embodiment directly generates power when an alcohol is brought into contact with the electrode catalyst and oxidized to produce a carboxylic acid in the anode.

FIG. 1 is a schematic diagram showing a schematic configuration of the fuel cell of the present embodiment.

As shown in FIG. 1, a fuel cell 10 of the present embodiment includes an anode 11, a cathode 12, and an electrolyte 13.

The anode 11 and the cathode 12 are arranged so as to face each other with the electrolyte 13 in between. Further, the anode 11 and the cathode 12 are electrically connected to each other via a conducting wire 20 and a voltmeter 21.

The anode 11 is also called a fuel electrode.

The anode 11 is mainly composed of a porous electrically conductive solid, and is provided with the electrode catalyst of the present embodiment on the surface or inside thereof, or on the electrolyte 13 side (the side opposite to the cathode 12 side) of the anode 11. The anode 11 is provided with an anode catalyst layer (not shown) composed of the electrode catalyst of the present embodiment on the electrolyte 13 side.

The cathode 12 is also called an air electrode.

The cathode 12 is mainly composed of a catalyst for reducing oxygen and an electrode.

The electrolyte 13 is a proton conductive membrane such as Nafion exhibiting high proton conductivity.

An example of a power generation method by the fuel cell 10 of the present embodiment will be described.

Here, the power generation method by the fuel cell 10 will be described by exemplifying a case where lactic acid serving as an alcohol is brought into contact with the catalyst of the present embodiment to be oxidized, thereby generating pyruvic acid which is a carboxylic acid.

As shown in FIG. 1, when lactic acid (LA) is supplied to the anode 11 side, the anode catalyst layer provided on one surface 11a of the anode 11 comes into contact with the lactic acid, whereby the lactic acid is oxidized to produce pyruvic acid (PA). At this time, as shown in the following formula (2), hydrogen is desorbed from lactic acid to generate a hydrogen ion (H$^+$) and an electron (e$^-$).

$$H2 \rightarrow 2H^+ + 2e^- \tag{2}$$

Hydrogen ions (H$^+$) move in the electrolyte 13 and reach the cathode 12. Electrons (e$^-$) move in the external circuit (the conducting wire 20 and the voltmeter 21) and reach the cathode 12.

On the other hand, as shown in FIG. 1, when oxygen (O$_2$) is supplied to the cathode 12 side, the cathode 12 comes into contact with the oxygen (O$_2$), whereby the oxygen is reduced to produce water (H$_2$O). At this time, as shown in the following formula (3), hydrogen ions (H$^+$) and electrons (e$^-$) bond with oxygen (O$_2$) to generate water (H$_2$O).

$$\tfrac{1}{2}O_2 + 2H^+ + 2e^- \rightarrow H_2O \tag{3}$$

The fuel cell 10 generates power by repeating such a redox reaction.

Since the fuel cell of the present embodiment is provided with the electrode catalyst of the present embodiment on the surface or inside of the anode or on the electrolyte side in the anode, by supplying lactic acid to the anode side, it is possible to generate electricity when lactic acid is oxidized to synthesize pyruvic acid.

The fuel cell may form a so-called membrane electrode assembly composed of an anode, a cathode, and an electrolyte membrane.

Energy Recovery System

An energy recovery system of the present embodiment is a system that recovers energy of surplus electric power by reducing carboxylic acids to alcohols using surplus electric power and oxidizing alcohols to carboxylic acids.

The energy recovery system of the present embodiment includes: (a) a container for storing carboxylic acids; (b) a means for reducing carboxylic acids to alcohols using surplus electric power; (c) a means for storing the obtained alcohols; and (d) a means for oxidizing the aforementioned alcohols to produce the aforementioned carboxylic acids and generating electric power.

According to the energy recovery system of the present embodiment, it is possible to efficiently recover, without wasting, surplus electric power. For example, alcohols produced by using surplus electric power may be stored in a tank or the like at that place, or alcohols may be accumulated as an energy carrier from a single or a plurality of facilities, and they can be used to generate electric power using the fuel cell of the present invention. Further, when they are not used as an energy carrier, it is also possible to implement, in the form of, the production of useful materials by making use of low electric power. It should be noted that grid power and renewable power (solar power generation, wind power generation, hydroelectric power generation, geothermal power generation, biomass power generation, wave power generation, and the like) are called the first surplus power, and the recovered power is called the second surplus power.

Method for Producing Ketones and Carboxylic Acids

A method for producing ketones and carboxylic acids of the present embodiment is a method for synthesizing ketones and carboxylic acids by performing an electrochemical oxidation reaction of alcohols using the electrode catalyst of the present embodiment.

The method for oxidizing alcohols using the electrode catalyst of the present embodiment is not particularly limited, and examples thereof include a method in which the electrode catalyst supported on a base material (electrode) is brought into contact with alcohols, as in the fuel cell described above, and a method in which the electrode catalyst is brought into contact with alcohols by dispersing the electrode catalyst in a powder form in alcohols and stirring the resulting mixture of these.

Examples of the raw material alcohols used in the method for producing ketones and carboxylic acids of the present embodiment include α-hydroxy acids such as lactic acid, glycolic acid, 2-amino-2-hydroxyacetic acid, 2-hydroxy-3,3-dimethylbutanoic acid, 2-hydroxyvaleric acid, α-hydroxyglutaric acid, 2-hydroxysuccinic acid, phenyllactic acid, imidazole-4-lactic acid, 4-hydroxyphenyllactic acid and 2-hydroxy-4-methylvaleric acid.

Among secondary alcohols, alcohols containing a carboxyl group are preferable. Further, among the secondary alcohols, hydroxycarboxylic acids in which the secondary alcohol is a substituent at the α-position of the carboxyl group are more preferable.

By using secondary alcohols, ketones can be efficiently synthesized. Further, among secondary alcohols, ketones can be synthesized more efficiently by using alcohols containing a carboxyl group. Moreover, among secondary alcohols, ketones can be synthesized even more efficiently by using hydroxycarboxylic acids that are substituents at the α-position of the carboxyl group.

In the method for producing ketones and carboxylic acids of the present embodiment, since alcohols are oxidized using the electrode catalyst of the present embodiment, ketones and carboxylic acids can be efficiently synthesized.

A primary alcohol can also be used as the raw material in the present embodiment. Among primary alcohols, alcohols containing a carboxyl group are preferable. In particular, a hydroxycarboxylic acid in which the primary hydroxyl group is a substituent at the α-position of the carboxyl group is preferable. Examples of such a hydroxycarboxylic acid include glycolic acid.

Method for Producing Pyruvic Acid

A method for producing pyruvic acid of the present embodiment is a method for synthesizing pyruvic acid ($CH_3COCOOH$) by oxidizing lactic acid ($CH_3CH(OH)COOH$) using the electrode catalyst of the present embodiment.

The method for oxidizing lactic acid using the electrode catalyst of the present embodiment is not particularly limited, and examples thereof include a method in which the electrode catalyst supported on a base material (electrode) is brought into contact with lactic acid, as in the fuel cell described above, and a method in which the electrode catalyst is brought into contact with lactic acid by dispersing the electrode catalyst in a powder form in lactic acid and stirring the resulting mixture of these.

In the method for producing pyruvic acid of the present embodiment, since lactic acid is oxidized using the electrode catalyst of the present embodiment, pyruvic acid can be efficiently synthesized.

EXAMPLES

Hereinafter, the present invention will be described in more detail with reference to examples, but the present invention is not limited to the following examples.

Catalyst Preparation

Among the carbon-supported platinum-palladium alloy nanoparticle catalysts represented by the general formula $Pt_{(100-n)}Pd_n/C$, those having the respective compositions in which n=0, 20, 25, 50, 75 and 100 were synthesized by a reduction precipitation method using a personal organic synthesizer PPS-2511 manufactured by Tokyo Rikakikai Co., Ltd.

Example 1

30 mL of 2-ethoxyethanol, a 560.78 mmol/L $H_2PtCl_6$ aqueous solution (114 μL, 0.096 mmol), 214.4 mg (0.032 mmol) of Pd(OAc), and 5 mL of acetone were introduced into a test tube, and $H_2PtCl_6$ and $Pd(OAc)_2$ were sufficiently dissolved in the resulting solution by 15 minutes of ultrasonication.

Next, 100.0 mg of VULCAN (registered trademark) XC72R manufactured by Cabot Corporation was added to the obtained solution, and the contents were thoroughly mixed by ultrasonication for 10 minutes.

Then, the resulting mixture was stirred for 30 minutes at a rotation speed of 1,200 rpm while bubbling argon (Ar) gas.

After 30 minutes, the argon (Ar) bubbling was changed to flowing, and a solution obtained by dissolving 38.3 mg of sodium borohydride (1 mmol) in 25 mL of water was added dropwise with a Pasteur pipette over 15 minutes. At this time, the liquid temperature was kept at 15° C.

In order to allow the reaction to proceed sufficiently, the temperature was raised to 30° C. at a rate of temperature increase of 3° C./min and kept at 30° C. for 45 minutes.

Then, the resultant was allowed to cool to room temperature (20° C.) over 45 minutes. At this time, a product was generated in the test tube.

The product was separated from the solution by washing the product from the test tube into a centrifuge tube with 30 mL of acetone and centrifuging at 6,500 rpm for 3 minutes.

Furthermore, an operation of adding 30 mL of acetone and centrifuging at 6,500 rpm for 3 minutes was repeated twice.

Then, an operation of adding 30 mL of acetone and 5 mL of water and centrifuging at 6,500 rpm for 3 minutes was repeated twice.

Thereafter, 30 mL of acetone was added, and the product was washed into a flask by ultrasonication, subjected to suction filtration using a membrane filter H100A 047A (pore size: 1.0 μm, manufactured by ADVANTEC), washed three times with water, and three times with acetone, and vacuum dried for 12 hours using a desiccator.

After drying, a carbon-supported platinum-palladium alloy nanoparticle catalyst having a Pd content of 25 at % (atomic %) and a Pt content of 75 at % (atomic %) (hereinafter referred to as "$Pt_{75}Pd_{25}$/C catalyst") was obtained.

Hydrogen Reduction Treatment

The carbon-supported platinum-palladium alloy nanoparticle catalyst to be structurally analyzed was subjected to a hydrogen reduction treatment in a tube furnace in order to obtain the same state as that when the electrode was produced.

The carbon-supported platinum palladium alloy nanoparticle catalyst was placed in a tube furnace, and nitrogen ($N_2$) gas was passed through the tube furnace at 100 ppm for 15 minutes at 24.5° C. to replace the inside of the tube furnace with nitrogen ($N_2$) gas.

Next, hydrogen ($H_2$) gas was passed through the tube furnace at 100 ppm for 15 minutes to replace the inside of the tube furnace with hydrogen ($H_2$) gas.

Subsequently, the flow rate of hydrogen ($H_2$) gas was changed to 60 ppm, and the temperature was raised from 24.5° C. to 250° C. at a rate of temperature increase of 3.8° C. $min^{-1}$, held at 250° C. for 120 minutes, and was then naturally cooled to 24.5° C., thereby performing the hydrogen reduction treatment.

Finally, nitrogen ($N_2$) gas was passed through the tube furnace at 100 ppm for 15 minutes to replace the inside of the tube furnace with nitrogen ($N_2$) gas, and then the electrode was taken out of the tube furnace.

The particle size of the obtained $Pt_{75}Pd_{25}$/C catalyst on a TEM image was measured, which showed a result of 2.0 nm or more and 8.9 nm or less.

High Frequency Inductively Coupled Plasma Emission Spectroscopy (ICP-AES)

The content (% by mass) of $Pt_{75}Pd_{25}$ and the ratio of Pt and Pd in the obtained $Pt_{75}Pd_{25}$/C catalyst were measured by high frequency inductively coupled plasma emission spectroscopy (ICP-AES).

The metal contained in the $Pt_{75}Pd_{25}$/C catalyst was quantified by high frequency inductively coupled plasma emission spectroscopy (inductively coupled plasma-atomic emission spectroscopy, ICP-AES) using a Thermo Fisher SCIENTIFIC iCAP 6300 instrument.

3 mg of the $Pt_{75}Pd_{25}$/C catalyst was weighed and placed in a screw tube together with 3 mL of nitric acid, 9 mL of hydrochloric acid and a stirring bar, and was heated and stirred at 80° C. for 2 hours using a hot stirrer at a rotation speed of 120 rpm to prepare a solution containing the $Pt_{75}Pd_{25}$/C catalyst.

The obtained solution was filtered using a Minisart (registered trademark) RC15 syringe filter manufactured by Sartorius AG, and the filtered solution (filtrate) was made into a solution of about 10 ppm using a 100 mL volumetric flask.

A platinum standard solution for atomic absorption spectrometry (1,000 ppm) was diluted to prepare platinum solutions of 1 ppm, 10 ppm and 20 ppm, and a calibration curve was produced. Further, a nickel standard solution (1,000 ppm) was diluted to prepare nickel solutions of 1 ppm, 10 ppm and 20 ppm, and a calibration curve was produced. In addition, a palladium standard solution (1,000 ppm) was diluted to prepare palladium solutions of 1 ppm, 10 ppm and 20 ppm, and a calibration curve was produced.

The results are shown in Table 1.

Example 2

The same operation as in Example 1 was performed except that a 352.1 mmol/L (291 μL, 0.102 mmol) $H_2PtCl_6$ aqueous solution was used and 25.75 mg (0.0256 mmol) of Pd(OAc) was used in Example 1, to obtain a carbon-supported platinum-palladium alloy nanoparticle catalyst having a Pd content of 20 at % (atomic %) and a Pt content of 80 at % (atomic %) (hereinafter referred to as "$Pt_{80}Pd_{20}$/C catalyst").

An average particle size of the obtained $Pt_{80}Pd_{20}$/C catalyst was measured in the same manner as in Example 1, which showed a result of 2.6 nm or more and 8.8 nm or less.

The content (% by mass) of $Pt_{80}Pd_{20}$ and the ratio of Pt and Pd in the obtained $Pt_{80}Pd_{20}$/C catalyst were measured in the same manner as in Example 1. The results are shown in Table 1.

Example 3

The same operation as in Example 1 was performed except that a 352.1 mmol/L (219 μL, 0.064 mmol) $H_2PtCl_6$ aqueous solution was used and 214.37 mg (0.064 mmol) of Pd(OAc) was used in Example 1, to obtain a carbon-supported platinum-palladium alloy nanoparticle catalyst having a Pd content of 50 at % (atomic %) and a Pt content of 50 at % (atomic %) (hereinafter referred to as "$Pt_{50}Pd_{50}$/C catalyst").

The particle size of the obtained $Pt_{50}Pd_{50}$/C catalyst was measured in the same manner as in Example 1, which showed a result of 2.7 nm or more and 13.5 nm or less.

The content (% by mass) of $Pt_{50}Pd_{50}$ and the ratio of Pt and Pd in the obtained $Pt_{50}Pd_{50}$/C catalyst were measured in the same manner as in Example 1. The results are shown in Table 1.

Example 4

The same operation as in Example 1 was performed except that a 352.1 mmol/L (90.9 μL, 0.032 mmol) $H_2PtCl_6$ aqueous solution was used and 221.55 mg (0.096 mmol) of Pd(OAc) was used in Example 1, to obtain a carbon-supported platinum-palladium alloy nanoparticle catalyst having a Pd content of 75 at % (atomic %) and a Pt content of 25 at % (atomic %) (hereinafter referred to as "$Pt_{25}Pd_{75}$/C catalyst").

The particle size of the obtained $Pt_{25}Pd_{75}$/C catalyst was measured in the same manner as in Example 1, which showed a result of 2.7 nm or more and 7.7 nm or less.

The content (% by mass) of $Pt_{25}Pd_{75}$ and the ratio of Pt and Pd in the obtained $Pt_{25}Pd_{75}$/C catalyst were measured in the same manner as in Example 1. The results are shown in Table 1.

Example 5

The same operation as in Example 1 was performed except that a 352.1 mmol/L (364 μL, 0.128 mmol) H$_2$PtCl$_6$ aqueous solution was used and Pd(OAc)$_2$ was not used in Example 1, to obtain a carbon-supported platinum-palladium alloy nanoparticle catalyst having a Pd content of 0 at % (atomic %) and a Pt content of 100 at % (atomic %) (hereinafter referred to as "Pt/C catalyst").

The particle size of the obtained Pt/C catalyst was measured in the same manner as in Example 1, which showed a result of 2.6 nm or more and 21.2 nm or less.

The content (% by mass) of Pt and the ratio of Pt and Pd in the obtained Pt/C catalyst were measured in the same manner as in Example 1. The results are shown in Table 1.

Example 6

The same operation as in Example 1 was performed except that 228.74 mg (0.128 mmol) of Pd(OAc) was used and a H$_2$PtCl$_6$ aqueous solution was not used in Example 1, to obtain a carbon-supported platinum-palladium alloy nanoparticle catalyst having a Pd content of 100 at % (atomic %) and a Pt content of 0 at % (atomic %) (hereinafter referred to as "Pd/C catalyst").

The particle size of the obtained Pd/C catalyst was measured in the same manner as in Example 1, which showed a result of 2.8 nm or more and 10.6 nm or less.

The content (% by mass) of Pd and the ratio of Pt and Pd in the obtained Pd/C catalyst were measured in the same manner as in Example 1. The results are shown in Table 1.

TABLE 1

| | Catalyst composition | Content of Pt$_{(100-n)}$Pd$_n$ [% by mass] | Ratio of Pt and Pd [atomic ratio] Pt | Pd |
|---|---|---|---|---|
| Production Example 5 | Pt/C | 21.1 | 100 | — |
| Production Example 2 | Pt$_{80}$Pd$_{20}$/C | 17.6 | 81 | 19 |
| Production Example 1 | Pt$_{75}$Pd$_{25}$/C | 13.1 | 73 | 27 |
| Production Example 3 | Pt$_{50}$Pd$_{50}$/C | 13.5 | 50 | 50 |
| Production Example 4 | Pt$_{25}$Pd$_{75}$/C | 12.8 | 23 | 77 |
| Production Example 6 | Pd/C | 9.5 | — | 100 |

From the results shown in Table 1, it was confirmed that the carbon-supported platinum-palladium alloy nanoparticle catalysts of Examples 1 to 6 had almost the same composition ratios as the composition ratios of those charged.

Powder X-Ray Diffraction (XRD) Measurement

A carbon-supported platinum-palladium alloy nanoparticle catalyst that had been subjected to a hydrogen reduction treatment was placed, in a boro-silicate capillary having an inner diameter of 0.5 mm manufactured by WJM-Glas/Muller GmbH, up to a position of about 7 mm inside from an end (opening), and in a state of being installed in a vacuum system and deaerated, an end portion of the capillary was sealed using a gas burner.

With respect to the capillary containing the carbon-supported platinum-palladium alloy nanoparticle catalyst that had been sealed, a powder X-ray diffraction (XRD) pattern was measured using a large synchrotron radiation facility SPring-8 BL44B2, at a wavelength λ=0.69035 Å (6.9035×10$^{-11}$ m). The obtained XRD pattern is shown in FIG. 2.

Figure 2:
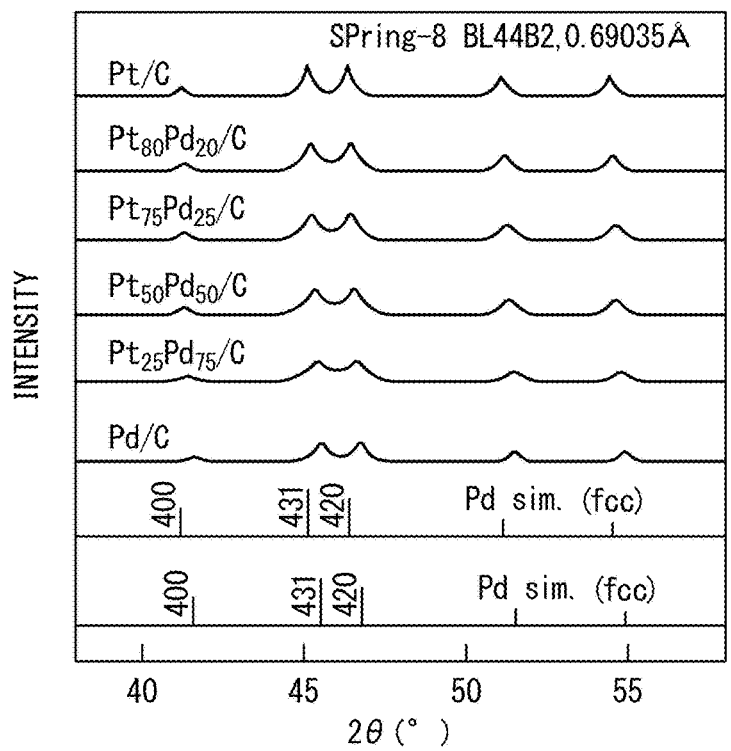
FIG. 2 is a diagram showing an XRD pattern of a carbon-supported platinum-palladium alloy nanoparticle catalyst.

As shown in FIG. 2, when the obtained XRD pattern was compared with the simulation result of Pt having an fcc structure (hereinafter, referred to as "Pt sim.") and the simulation result of Pd having an fcc structure (hereinafter, referred to as "Pd sim.") calculated using a wavelength λ=6.9035×10$^{-11}$ m, since the obtained XRD pattern is attributed to the pattern of the fcc structure, it was confirmed that the carbon-supported platinum-palladium alloy nanoparticle catalysts of Examples 1 to 6 had fcc structures, and that diffraction peaks shifted so as to approach the diffraction peak of Pd/C as the composition ratios of Pd increased.

The XRD measurement was performed on platinum black (platinum content: above 98.0%) manufactured by Kanto Chemical Co., Inc. and palladium black (powder, palladium content: above 99.95%) manufactured by Kojima Chemicals Co., Ltd. as reference samples, in the same manner as in the case of carbon-supported platinum-palladium alloy nanoparticle catalysts. Hereinafter, the platinum reference sample will be referred to as "Pt ref." and the palladium reference sample will be referred to as "Pd ref.".

Figure 3:
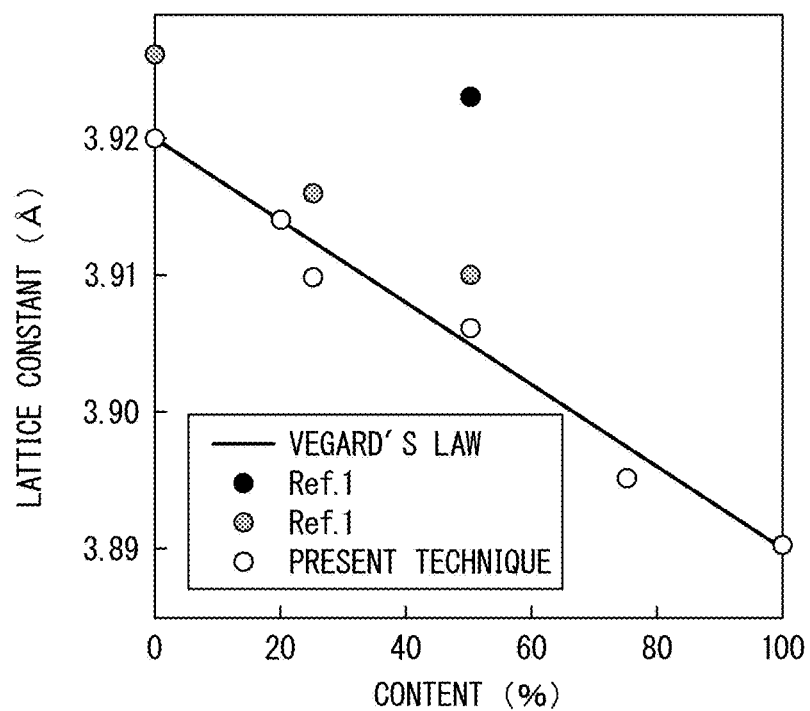
FIG. 3 is a diagram in which a lattice constant is plotted against a composition ratio of the carbon-supported platinum-palladium alloy nanoparticle catalyst.

The sample was identified by analyzing the obtained XRD pattern using the Rietveld method. At this time, with respect to a Debye-Scherrer optical system, the calculation was performed with the peak type PVII and an LP factor of 90. Table 2 shows the structural parameters calculated by the Rietveld analysis, and FIG. 3 shows a diagram in which the lattice constants are plotted against the composition ratios of the carbon-supported platinum-palladium alloy nanoparticle catalysts.

TABLE 2

| | Catalyst composition | Lattice constant [×10$^{-10}$ m] |
|---|---|---|
| Production Example 5 | Pt/C | 3.92172 |
| Production Example 2 | Pt$_{80}$Pd$_{20}$/C | 3.91415 |
| Production Example 1 | Pt$_{75}$Pd$_{25}$/C | 3.90987 |
| Production Example 3 | Pt$_{50}$Pd$_{50}$/C | 3.90623 |
| Production Example 4 | Pt$_{25}$Pd$_{75}$/C | 3.89524 |
| Production Example 6 | Pd/C | 3.89041 |
| Pt ref. | — | 3.91901 |
| Pd ref. | — | 3.89046 |

From the results of Table 2, the calculated lattice constants of the Pt/C catalyst and the Pd/C catalyst substantially coincided with the lattice constants of Pt ref. and Pd ref. On the other hand, it became clear that the lattice constant of the carbon-supported platinum-palladium alloy nanoparticle catalyst changed linearly with the composition ratio. Further, from the results of FIG. 3, it was confirmed that the carbon-supported platinum-palladium alloy nanoparticle catalysts followed Vegard's law.

Transmission Electron Microscope (TEM) Observation

Three drops of a solution obtained by dispersing a sample (carbon-supported platinum-palladium alloy nanoparticle catalyst) of about one spoonful of micro spatula in 3 mL of methanol were added dropwise onto an ester support membrane U1009 manufactured by EM Japan Co., Ltd. using a Pasteur pipette, and then dried to produce a sample grid.

Figure 4:
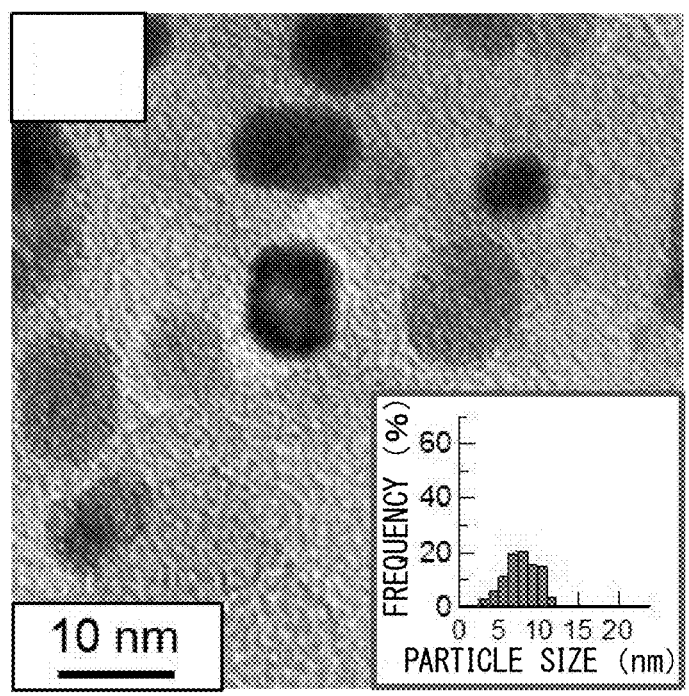
FIG. 4 is a diagram showing a transmission electron microscope image and a particle size distribution of a Pt/C catalyst of Example 5.
Figure 5:
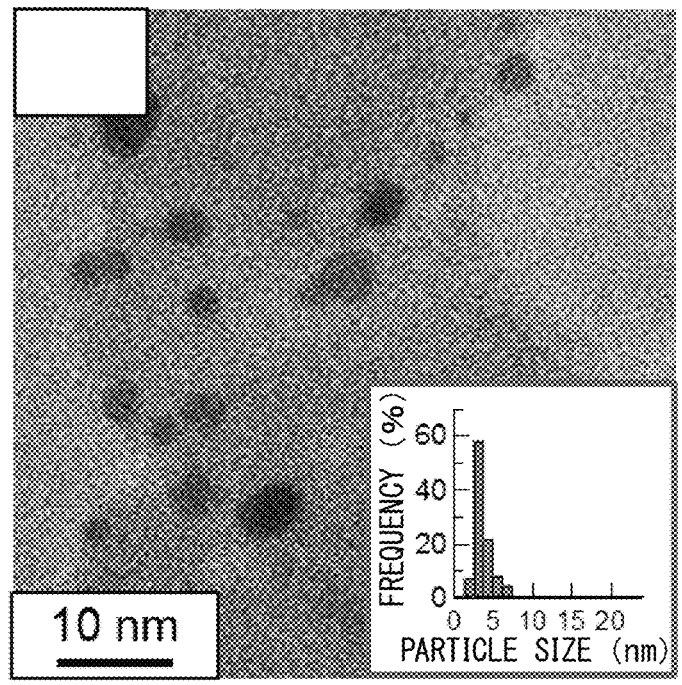
FIG. 5 is a diagram showing a transmission electron microscope image and a particle size distribution of a $Pt_{80}Pd_{20}$/C catalyst of Example 2.
Figure 6:
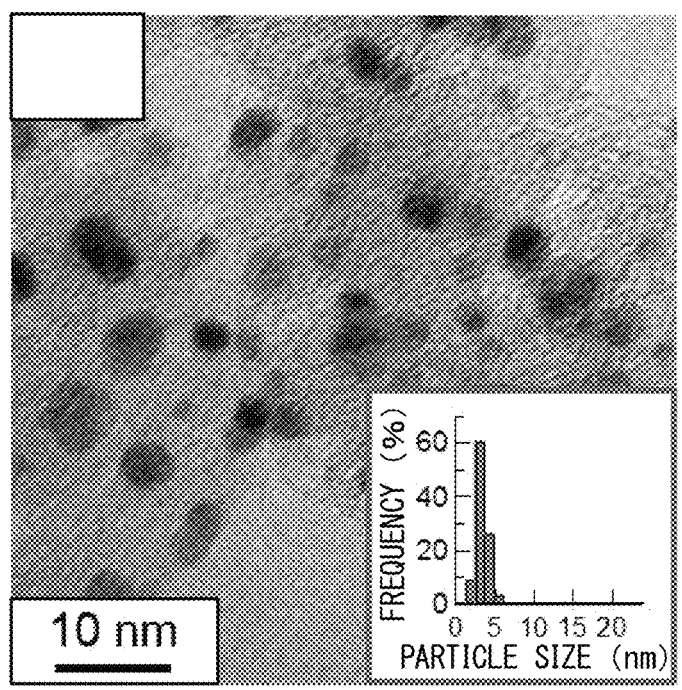
FIG. 6 is a diagram showing a transmission electron microscope image and a particle size distribution of a $Pt_{75}Pd_{25}$/C catalyst of Example 1.
Figure 7:
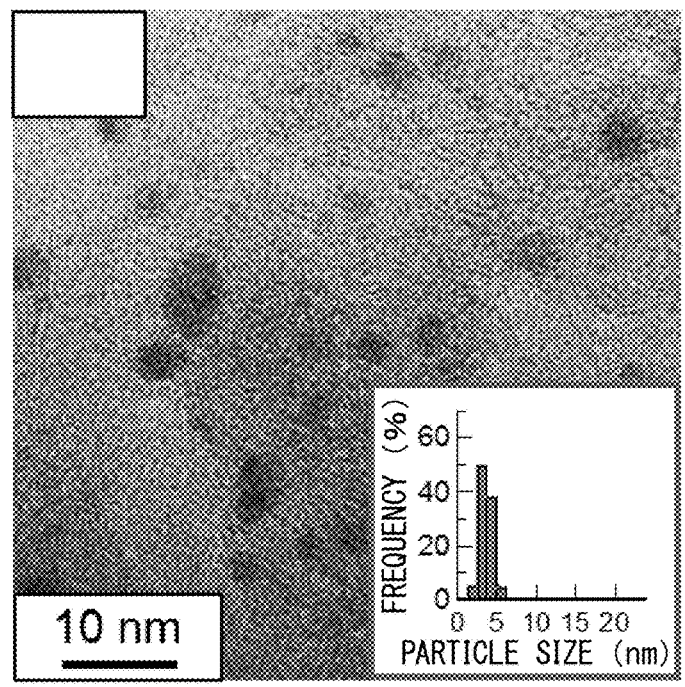
FIG. 7 is a diagram showing a transmission electron microscope image and a particle size distribution of a $Pt_{50}Pd_{50}$/C catalyst of Example 3.
Figure 8:
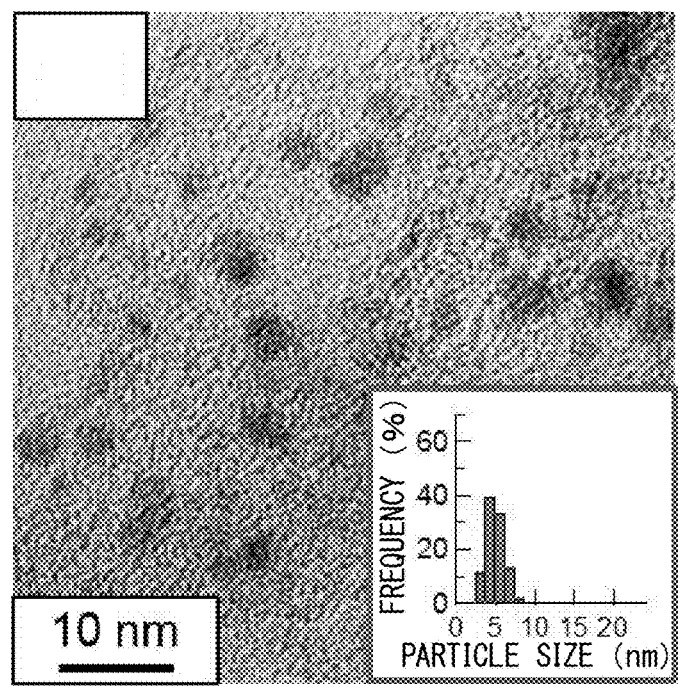
FIG. 8 is a diagram showing a transmission electron microscope image and a particle size distribution of a $Pt_{25}Pd_{75}$/C catalyst of Example 4.
Figure 9:
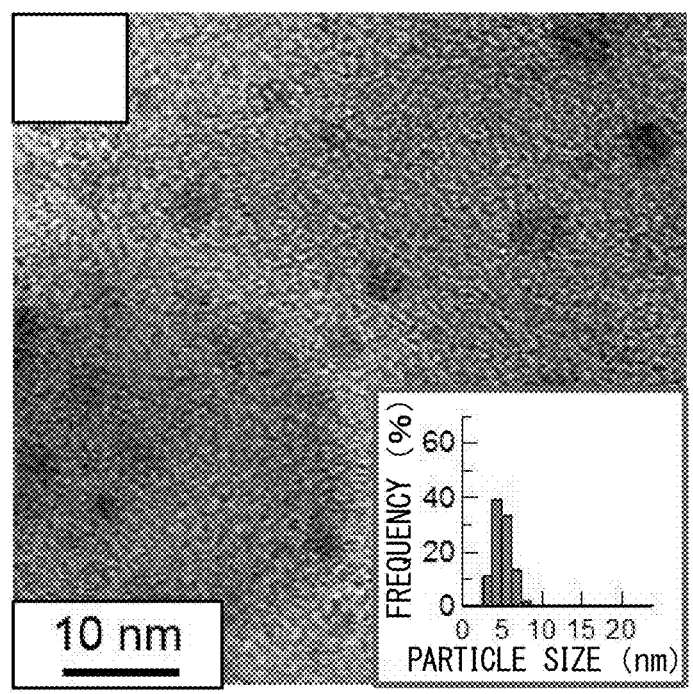
FIG. 9 is a diagram showing a transmission electron microscope image and a particle size distribution of a Pd/C catalyst of Example 6.

A transmission electron microscope (TEM) image of the sample was taken using a transmission electron microscope (JEM-2100HC manufactured by JEOL Ltd., at 200 kV). Further, diameters of about 150 particles in the transmission electron microscope image were measured, and the particle size dispersion and the average particle size were calculated. The results are shown in FIGS. 4 to 9 and Table 3. FIG. 4 is a diagram showing a transmission electron microscope image and a particle size distribution of the Pt/C catalyst of Example 5. FIG. 5 is a diagram showing a transmission electron microscope image and a particle size distribution of the Pt$_{80}$Pd$_{20}$/C catalyst of Example 2. FIG. 6 is a diagram showing a transmission electron microscope image and a particle size distribution of the $Pt_{75}Pd_{25}$/C catalyst of Example 1. FIG. 7 is a diagram showing a transmission electron microscope image and a particle size distribution of the $Pt_{50}Pd_{50}$/C catalyst of Example 3. FIG. 8 is a diagram showing a transmission electron microscope image and a particle size distribution of the $Pt_{25}Pd_{75}$/C catalyst of Example 4. FIG. 9 is a diagram showing a transmission electron microscope image and a particle size distribution of the Pd/C catalyst of Example 6. Table 3 shows the average particle sizes of the carbon-supported platinum-palladium alloy nanoparticles.

TABLE 3

| | Catalyst composition | Average particle size [nm] |
|---|---|---|
| Production Example 5 | Pt/C | 7.8 ± 2.7 |
| Production Example 2 | $Pt_{80}Pd_{20}$/C | 4.3 ± 1.3 |
| Production Example 1 | $Pt_{75}Pd_{25}$/C | 4.2 ± 1.0 |
| Production Example 3 | $Pt_{50}Pd_{50}$/C | 3.2 to 5.8 |
| | | 4.5 ± 1.3 |
| Production Example 4 | $Pt_{25}Pd_{75}$/C | 3.7 to 5.9 |
| | | 4.8 ± 1.1 |
| Production Example 6 | Pd/C | 3.9 to 6.3 |
| | | 5.1 ± 1.2 |

Scanning Transmission Electron Microscope (STEM) Observation, Energy Dispersive X-Ray Spectroscopy (EDS) Measurement Three drops of a dispersion liquid obtained by dispersing a sample (carbon-supported platinum-palladium alloy nanoparticle catalyst) of about one spoonful of micro spatula in 3 mL of methanol were added dropwise onto a microgrid (NP-C10 STEM Cu100P) manufactured by Okenshoji Co., Ltd. using a Pasteur pipette, and then dried to produce a sample grid.

Figure 10:
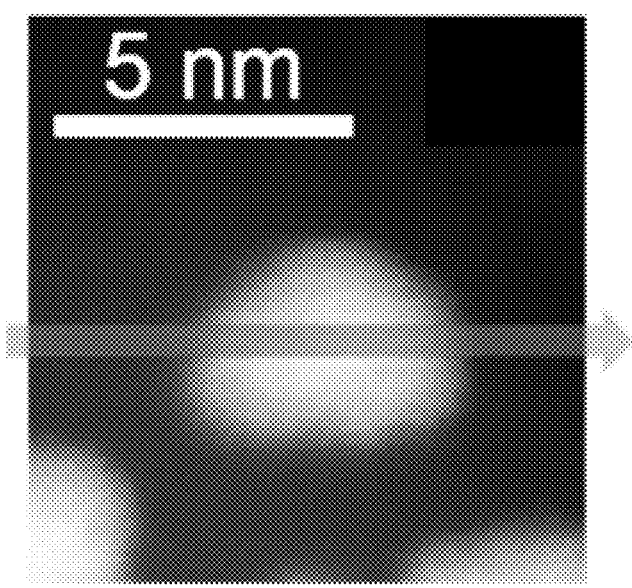
FIG. 10 is a diagram showing a result of STEM-EDS regarding carbon-supported platinum-palladium alloy nanoparticles of Example 2.
Figure 11:
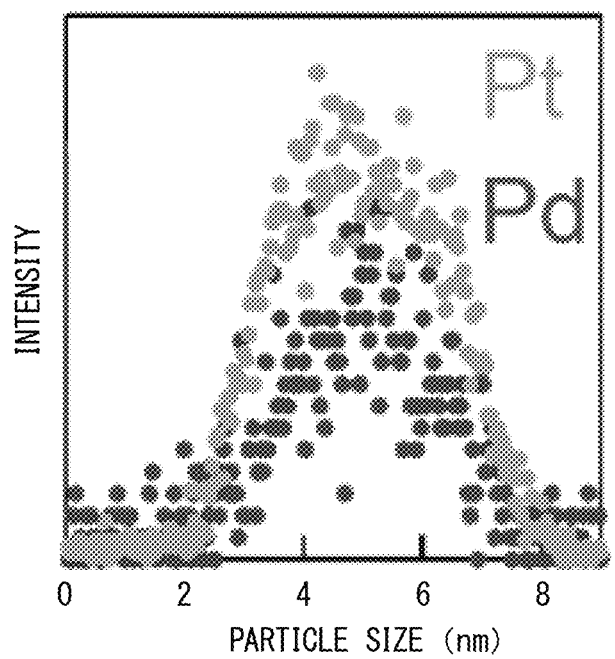
FIG. 11 is a diagram showing the result of STEM-EDS regarding the carbon-supported platinum-palladium alloy nanoparticles of Example 2, and is a diagram showing a result of performing a line scan in an arrow portion in FIG. 10.
Figure 12:
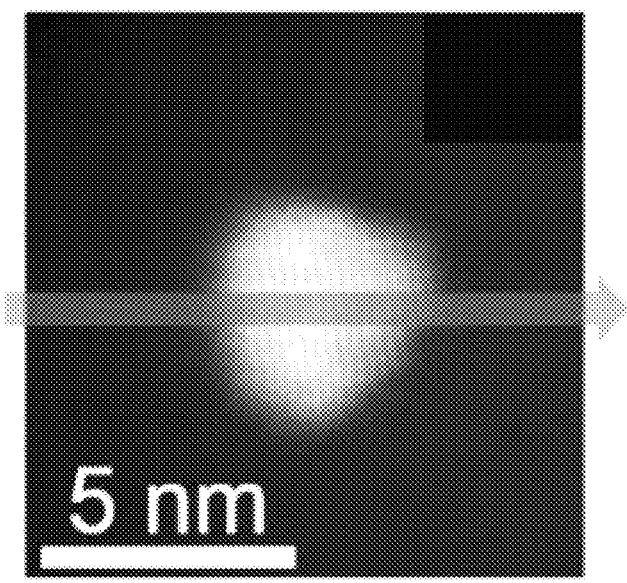
FIG. 12 is a diagram showing a result of STEM-EDS regarding carbon-supported platinum-palladium alloy nanoparticles of Example 1.
Figure 13:
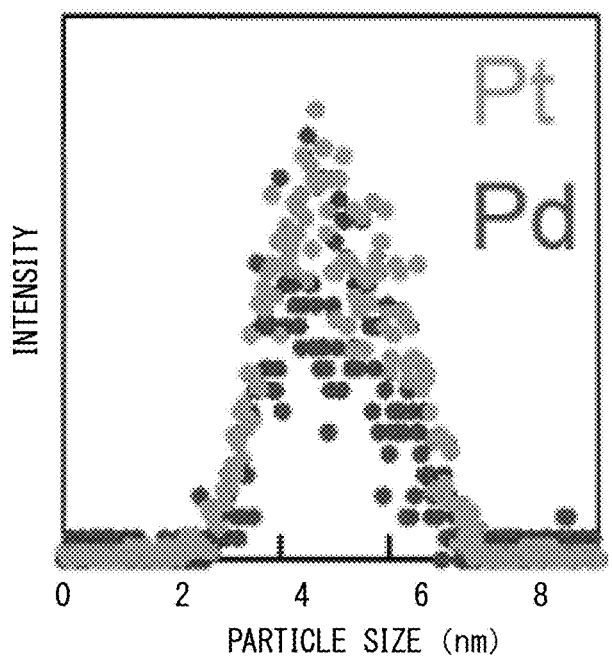
FIG. 13 is a diagram showing the result of STEM-EDS regarding the carbon-supported platinum-palladium alloy nanoparticles of Example 1, and is a diagram showing a result of performing a line scan in an arrow portion in FIG. 12.
Figure 14:
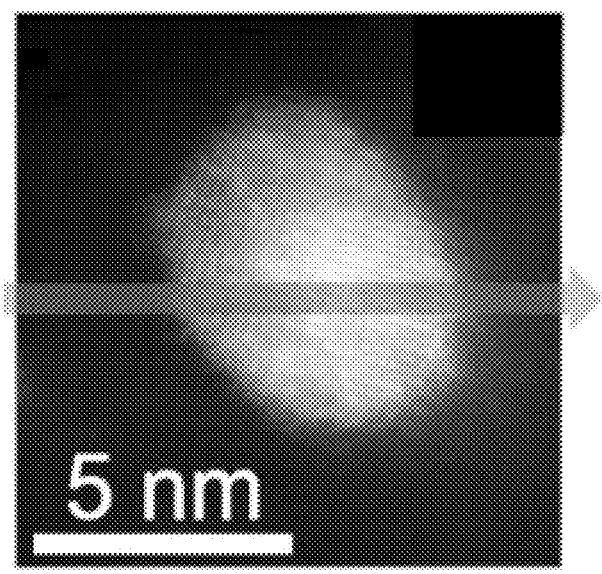
FIG. 14 is a diagram showing a result of STEM-EDS regarding carbon-supported platinum-palladium alloy nanoparticles of Example 3.
Figure 15:
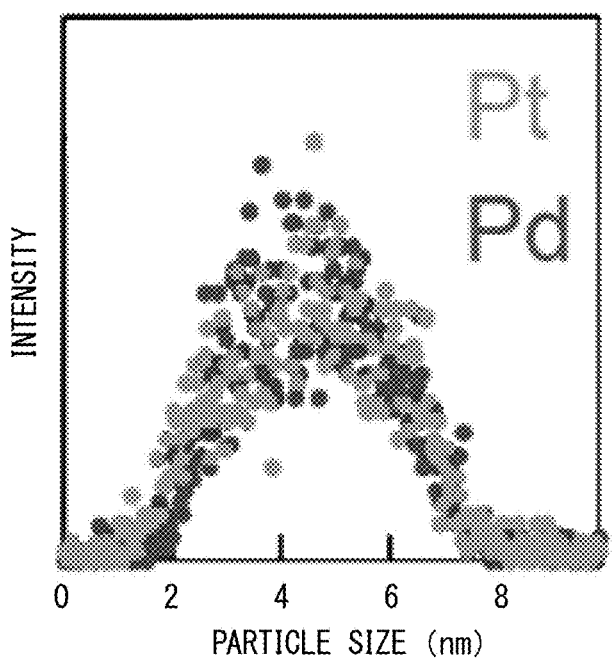
FIG. 15 is a diagram showing the result of STEM-EDS regarding the carbon-supported platinum-palladium alloy nanoparticles of Example 3, and is a diagram showing a result of performing a line scan in an arrow portion in FIG. 14.
Figure 16:
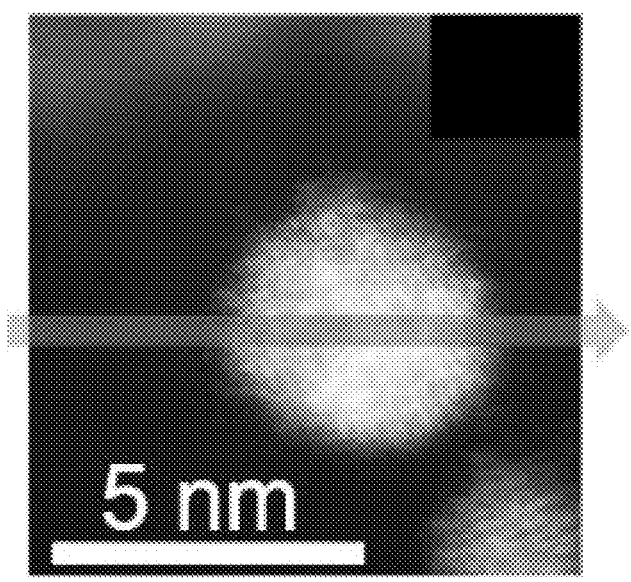
FIG. 16 is a diagram showing a result of STEM-EDS regarding carbon-supported platinum-palladium alloy nanoparticles of Example 4.
Figure 17:
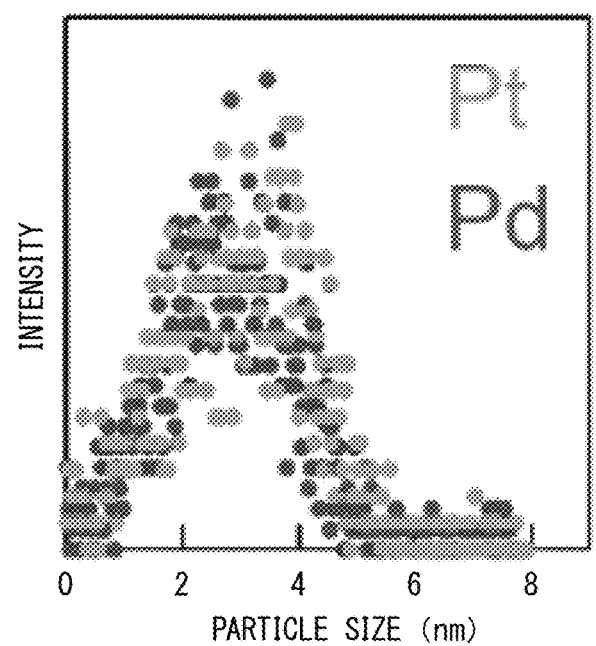
FIG. 17 is a diagram showing the result of STEM-EDS regarding the carbon-supported platinum-palladium alloy nanoparticles of Example 4, and is a diagram showing a result of performing a line scan in an arrow portion in FIG. 16.

A line scan was performed by energy dispersive X-ray spectroscopy using a scanning transmission electron microscope (JEM-ARM200F manufactured by JEOL Ltd., at 200 kV) (scanning transmission electron microscopy-energy dispersive spectroscopy, STEM-EDS). The results are shown in FIGS. 10 to 17. FIGS. 10 and 11 are diagrams showing the results of STEM-EDS regarding the carbon-supported platinum-palladium alloy nanoparticles of Example 2. FIG. 11 is a diagram showing a result of performing a line scan in an arrow portion in FIG. 10. FIGS. 12 and 13 are diagrams showing the results of STEM-EDS regarding the carbon-supported platinum-palladium alloy nanoparticles of Example 1. FIG. 13 is a diagram showing a result of performing a line scan in an arrow portion in FIG. 12. FIGS. 14 and 15 are diagrams showing the results of STEM-EDS regarding the carbon-supported platinum-palladium alloy nanoparticles of Example 3. FIG. 15 is a diagram showing a result of performing a line scan in an arrow portion in FIG. 14. FIGS. 16 and 17 are diagrams showing the results of STEM-EDS regarding the carbon-supported platinum-palladium alloy nanoparticles of Example 4. FIG. 17 is a diagram showing a result of performing a line scan in an arrow portion in FIG. 16.

From the results of FIGS. 10 to 17, it is considered that the carbon-supported platinum-palladium alloy nanoparticles carbon of Examples 1 to 4 are alloys in which Pt and Pd are thoroughly mixed, because Pt and Pd are distributed in a similar manner.

X-Ray Photoelectron Spectroscopy (XPS)

The constituent elements of samples (carbon-supported platinum-palladium alloy nanoparticle catalysts) and their electronic states were analyzed by X-ray photoelectron spectroscopy (XPS) using an ULVAC-PHI PHI5000 VersaProbe II (AlKα radiation, 1486.6 eV) manufactured by ULVAC-PHI, Inc.

Figure 18:
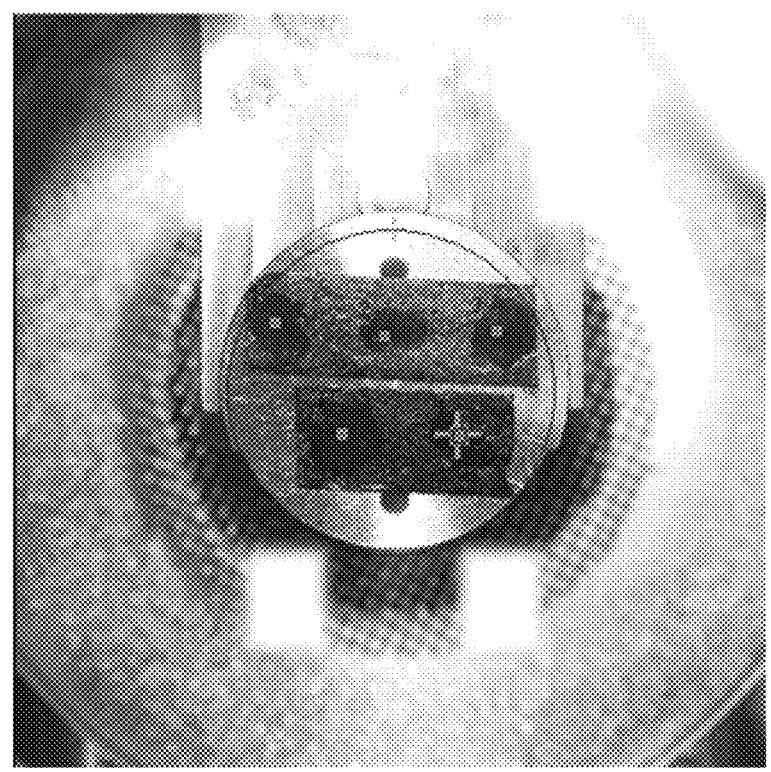
FIG. 18 is an optical photograph showing a method of fixing a carbon-supported platinum-palladium alloy nanoparticle catalyst to a sample holder in the analysis by X-ray photoelectron spectroscopy.

As shown in FIG. 18, a carbon tape was attached to the sample holder, and the sample was placed on the carbon tape.

After confirming that the sample did not peel off from the carbon tape and introducing the sample holder into an apparatus chamber, the inside of the apparatus chamber was evacuated to perform XPS measurements.

Figure 19:
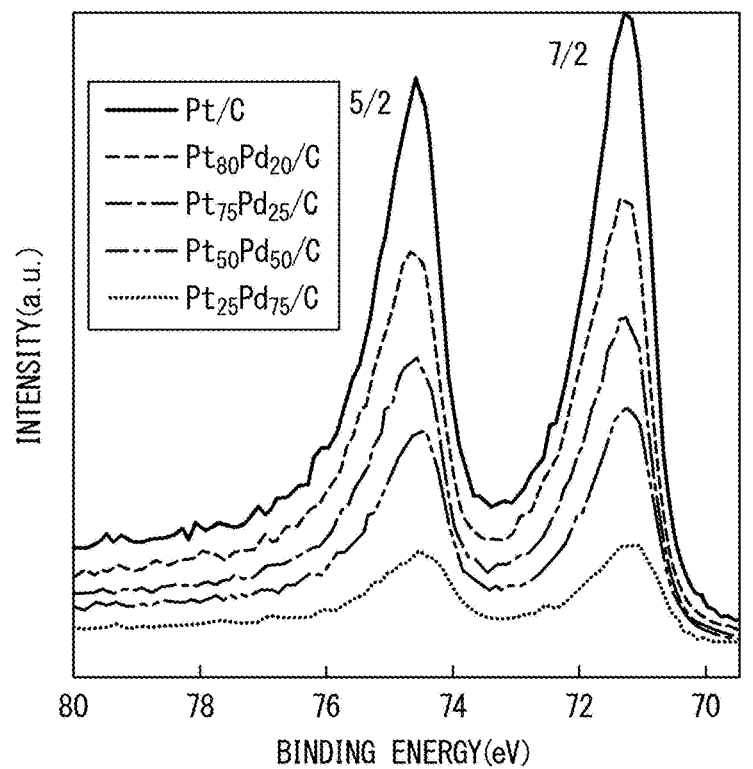
FIG. 19 is a diagram showing XPS spectra of electrons in the $4f_{7/2}$ orbital and $4f_{5/2}$ orbital of Pt.
Figure 20:
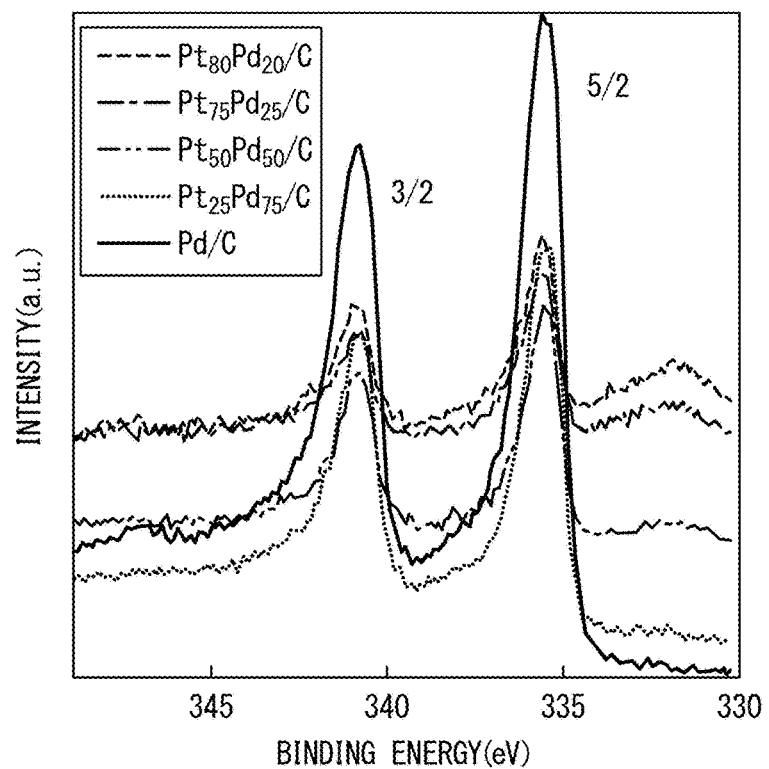
FIG. 20 is a diagram showing XPS spectra of electrons in the $3d_{5/2}$ orbital and $3d_{3/2}$ orbital of Pd.
Figure 21:
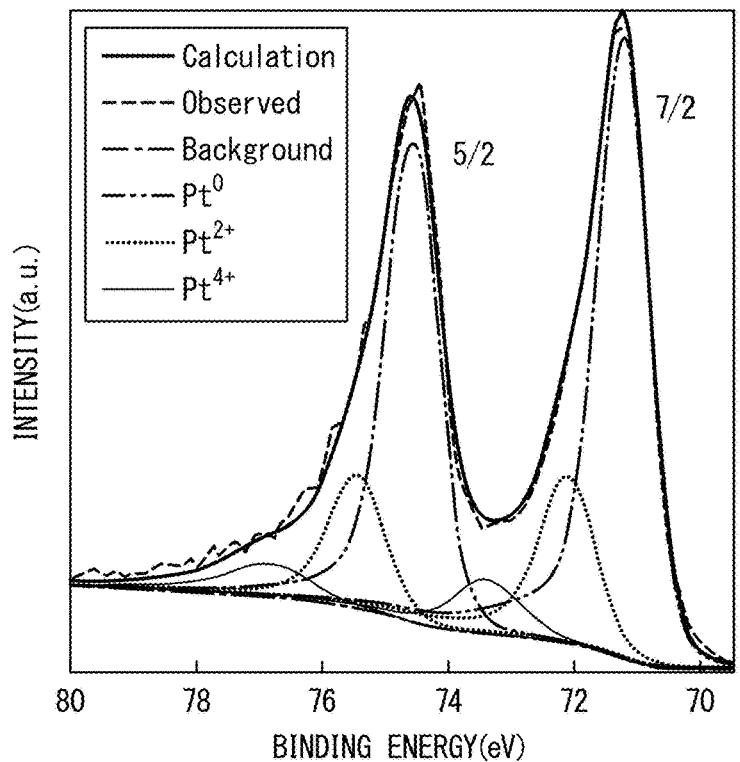
FIG. 21 is a diagram showing a result of analysis of XPS spectra of electrons in the $4f_{7/2}$ orbital and $4f_{5/2}$ orbital of Pt.
Figure 22:
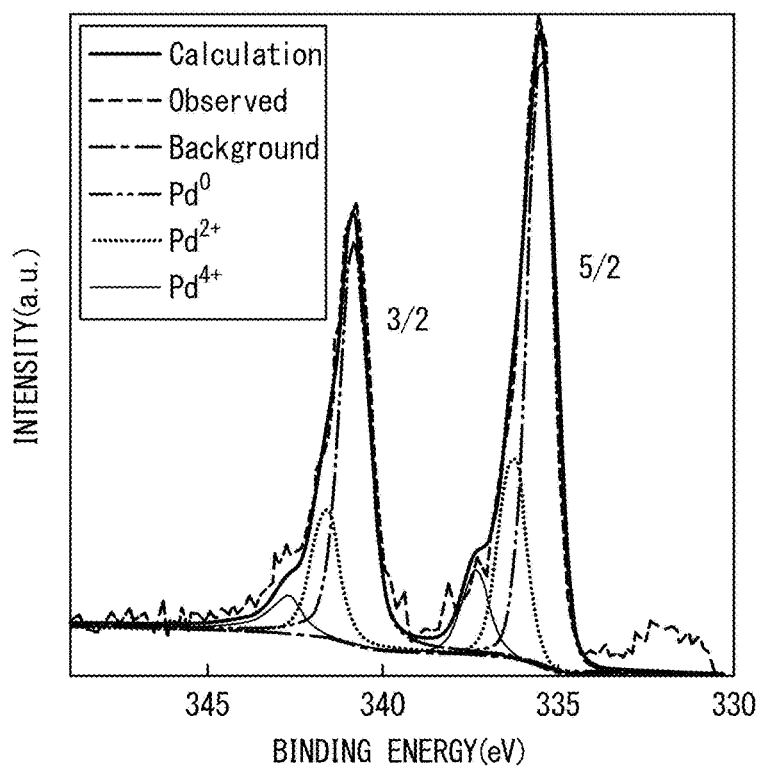
FIG. 22 is a diagram showing a result of analysis of XPS spectra of electrons in the $3d_{5/2}$ orbital and $3d_{3/2}$ orbital of Pd.

The obtained XPS spectra were calibrated so that the peak binding energies derived from C1s of carbon were 284.5 eV. The measurement was performed by targeting the spectrum mainly composed of the electrons of the $4f_{7/2}$ orbital and $4f_{5/2}$ orbital from which the strongest intensity is obtained, regarding the XPS spectrum derived from Pt in each sample, and targeting the spectrum mainly composed of the electrons of the $3d_{5/2}$ orbital and $3d_{3/2}$ orbital from which the strongest intensity is obtained, regarding the XPS spectrum derived from Pd. In performing curve fitting analysis of the obtained spectra, the analysis was performed using a least squares method by assuming that $Pt^0$, $Pt^{2+}$ and $Pt^{4+}$ components were present in Pt in the sample, and that $Pd^0$, $Pd^{2+}$ and $Pd^{4+}$ components were present in Pd. The results are shown in FIGS. 19 to 22. FIG. 19 is a diagram showing XPS spectra of electrons in the $4f_{7/2}$ orbital and $4f_{5/2}$ orbital of Pt. FIG. 20 is a diagram showing XPS spectra of electrons in the $3d_{5/2}$ orbital and $3d_{3/2}$ orbital of Pd. FIG. 21 is a diagram showing a result of analysis of XPS spectra of electrons in the $4f_{7/2}$ orbital and $4f_{5/2}$ orbital of Pt. FIG. 22 is a diagram showing a result of analysis of XPS spectra of electrons in the $3d_{5/2}$ orbital and $3d_{3/2}$ orbital of Pd.

Further, Table 4 shows the calculated binding energies of the $Pt^0$ $4f_{7/2}$ orbital and Pd $3d_{5/2}$ orbital.

TABLE 4

| | Catalyst composition | Binding energy of $4f_{7/2}$ orbital of $Pt^0$ [eV] | Binding energy of $3d_{5/2}$ orbital of Pd [eV] |
|---|---|---|---|
| Production Example 5 | Pt/C | 71.15 | — |
| Production Example 2 | $Pt_{80}Pd_{20}$/C | 71.20 | 335.50 |
| Production Example 1 | $Pt_{75}Pd_{25}$/C | 71.27 | 335.56 |
| Production Example 3 | $Pt_{50}Pd_{50}$/C | 71.21 | 335.45 |
| Production Example 4 | $Pt_{25}Pd_{75}$/C | 71.09 | 335.33 |
| Production Example 6 | Pd/C | — | 335.25 |

From the results of Table 4, it was found that $Pt_{75}Pd_{25}$/C exhibited the maximum values for the binding energy of the $4f_{7/2}$ orbital of $Pt^0$ and the binding energy of the $3d_{5/2}$ orbital of Pd, as compared with the other compositions. From these results, it was confirmed that $Pt_{75}Pd_{25}$/C had a stronger electronic interaction between Pt and Pd, as compared with the other compositions.

Measurement of XPU

UPS measurements were performed in order to determine the work function of the catalysts. For the UPS measurement, the measurement was performed using an electron spectroscopy analyzer (Versa Probe II, ULVAC-PHI) with the HeI line in a state where a Pd—Pt/C powder sample was placed on a measurement stage, a gold wire was placed thereon, and a mask was further attached and fixed.

Figure 23:
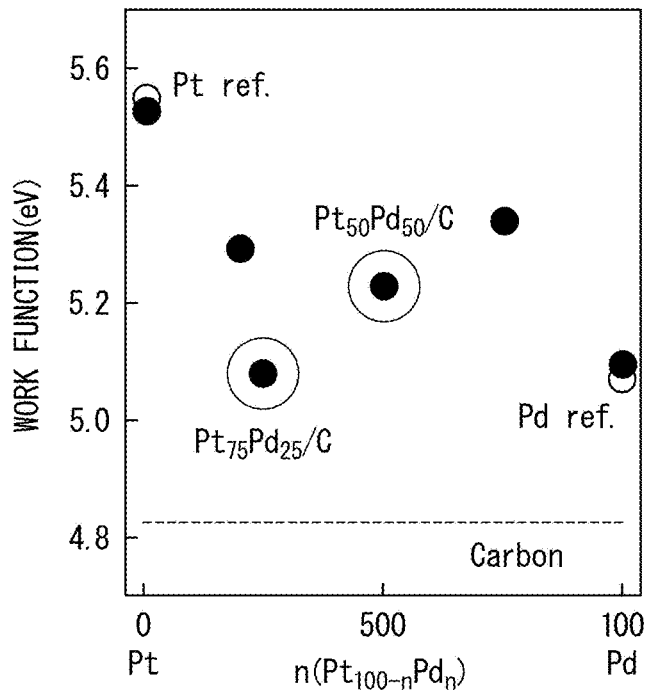
FIG. 23 is a diagram showing a work function obtained by analyzing a UPS spectrum measured by applying a bias of −0.6 V to a sample.

The work function obtained by analyzing the UPS spectrum measured by applying a bias of −0.6 V to a sample is shown in Table 5 and FIG. 23. From Table 5 and FIG. 23, it became clear that the work functions of Pd—Pt/C catalysts varied depending on the composition, and all had a work function smaller than that of Pt.

Table 6 shows the work functions of simple metals.

TABLE 5

| Catalyst | Work function (eV) |
| --- | --- |
| Pt/C | 5.525 |
| $Pt_{80}Pd_{20}$/C | 5.295 |
| $Pt_{75}Pd_{25}$/C | 5.08 |
| $Pt_{50}Pd_{50}$/C | 5.23 |
| $Pt_{25}Pd_{75}$/C | 5.34 |

TABLE 6

| Metal | Work function (eV) |
| --- | --- |
| Ru | 4.71 |
| Rh | 4.98 |
| Pd | 5.12 |
| Ag | 4.26 |
| Ir | 5.27 |
| Pt | 5.65 |
| Au | 5.1 |

From Table 6, it can be seen that the work functions of the metals in the fifth period are larger than those of the metals in the fourth period, and even among the metals in the same period, the work functions of Ag and Au in which electrons at the Fermi level are on the s-orbital are smaller than those of other metals. Therefore, in the Pd—Pt/C catalysts, it is considered that electrons move from Pd having a small work function to Pt having a large work function. As a result, since the nuclear charge per electron on Pt (the force with which the atomic nucleus of Pt attracts an electron) decreases as the electron density on Pt increases, the work function of the alloy as a whole decreases. Although the amount of charge transfer between Pt and Pd varies depending on the coordination number of the metal element, the alloy structure, and the stability of the component metals, in the case of Pd—Pt/C catalysts, it is considered that the amount of charge transfer reaches a maximum value in the $Pt_{75}Pd_{25}$/C catalyst and its work function becomes a minimum value.

Figure 24:
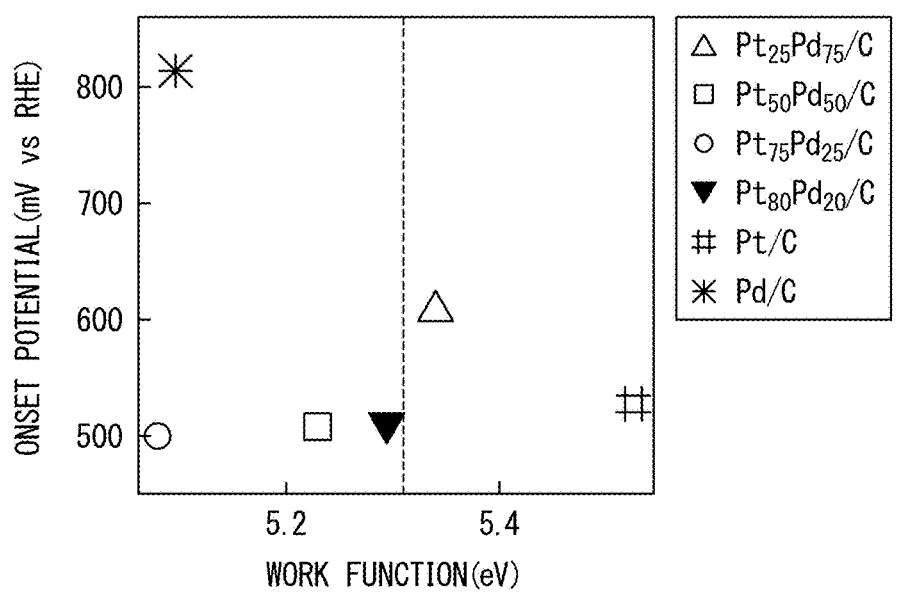
FIG. 24 is a diagram showing a relationship between the work function and the onset potential.

Next, FIG. 24 shows a relationship between the work function of PdPt obtained previously and the onset potential of the electrooxidation of lactic acid. As a result, it was revealed that Pd—Pt/C which has a work function smaller than the arithmetic mean of the work functions of Pt/C and Pd/C shown by the dotted line exhibits high activity for the electrochemical oxidation of alcohol. It is considered that this is because the electrochemical oxidation of alcohol requires strong interaction between the alcohol (hydroxyl group (—OH)) and the catalyst, so that Pt which strongly interacts with protons exhibits higher activity than Pd. Furthermore, it is considered that the alloy catalyst $Pt_{75}Pd_{25}$/C having a small work function has an ability to donate electrons to an antibonding orbital of the substrate, and therefore highly activates the substrate molecule and exhibits high catalytic activity.

Cyclic Voltammetry (CV) Measurement

Figure 25:
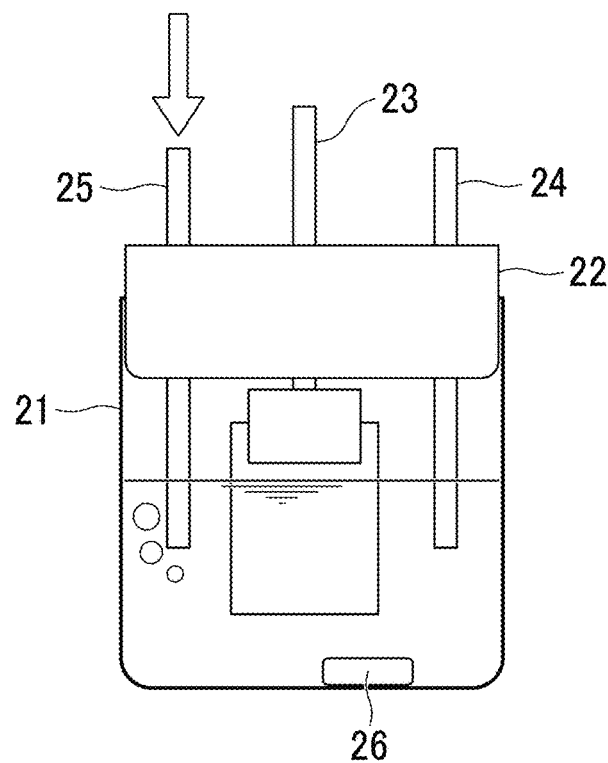
FIG. 25 is a schematic configuration diagram showing an electrochemical cell used for a CV measurement.
Figure 26:
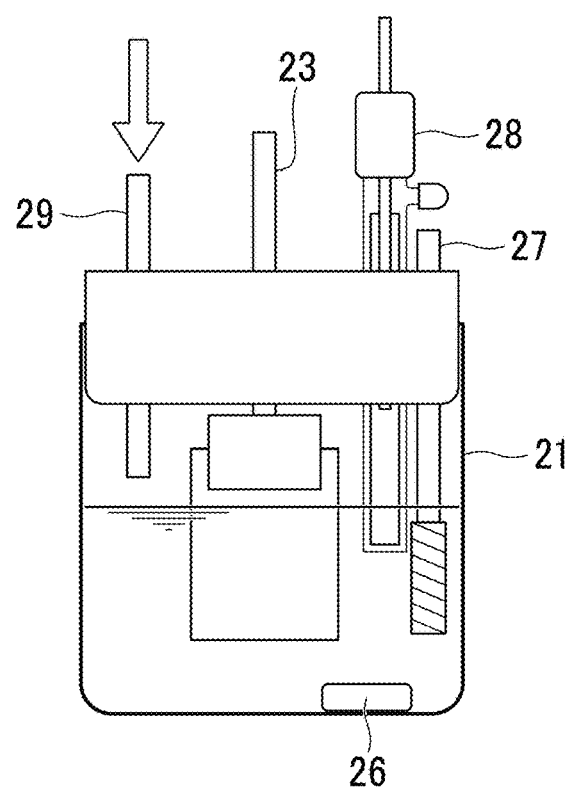
FIG. 26 is a schematic configuration diagram showing an electrochemical cell used for the CV measurement.

FIGS. 25 and 26 are schematic configuration diagrams showing an electrochemical cell used for a CV measurement.

In FIGS. 25 and 26, reference numeral 21 denotes a cell, reference numeral 22 denotes a sealing plug that seals the cell 21, reference numeral 23 denotes a working electrode, reference numeral 24 denotes a thermometer, reference numeral 25 denotes a first gas introduction pipe, reference numeral 26 denotes a stirring bar, reference numeral 27 denotes a counter electrode, reference numeral 28 denotes a reference electrode, and reference numeral 29 denotes a second gas introduction pipe.

As the working electrode 23, electrodes containing the carbon-supported platinum-palladium alloy nanoparticle catalysts of Examples 1 to 6 were installed. As the counter electrode 27, a platinum counter electrode (manufactured by BAS Inc.) having an electrode diameter of 0.5 mm and a length of 23 cm was used. As the reference electrode 28, an Ag/AgCl-saturated KCl silver-silver chloride reference electrode (manufactured by Inter Chemical Ltd.) was used. Further, as a potentiostat, VersaSTAT4 manufactured by Princeton Applied Research was used.

As a blank sample, a 0.2 mol/L sodium sulfate aqueous solution obtained by dissolving 14.20 g (0.1000 mol) of sodium sulfate in 500 mL of superelectrolyzed water was prepared, and a mixed aqueous solution containing 0.2 mol/L sodium sulfate and 30 mmol/L lactic acid obtained by dissolving 14.20 g (0.1000 mol) of sodium sulfate and 1.12 mL (15 mmol) of lactic acid in superelectrolyzed water so that the total volume was 500 mL was prepared.

The mixed aqueous solution was introduced into the cell 21 having a volume of 80 mL, and then, while bubbling an inert gas for 30 minutes, heated to a measurement temperature using a hot stirrer equipped with the stirring bar 26 while stirring at 300 rpm.

After 30 minutes, it was confirmed that the liquid temperature reached 70° C., a thermocouple portion part of Digital Fine Thermo DG2N manufactured by Hakko Electric Co., Ltd. was removed from the solution, and as shown in FIG. 26, the inert gas bubbling was switched to flowing.

Figure 27:
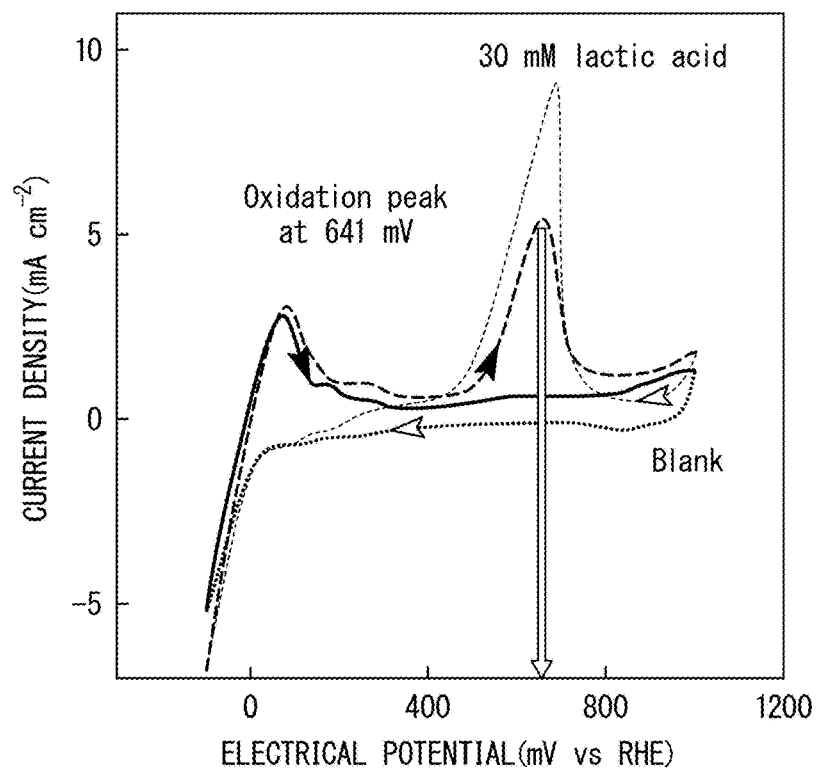
FIG. 27 is a diagram showing a result of the second cycle in a CV measurement on a Pt/C catalyst.

Each electrode was connected to Versastat 4 manufactured by Princeton Applied Research, and the CV measurement was performed for 3 cycles at a scan rate of 10 $mVs^{-1}$ in the range of −100 mV vs RHE to +1,000 mV vs RHE. The results are shown in FIG. 27. FIG. 27 is a diagram showing the result of the second cycle in the CV measurement on the Pt/C catalyst.

Regarding the mixed aqueous solution containing 30 mmol/L lactic acid, when the electrical potential was swept from negative to positive or from positive to negative, an oxidation peak not found in the blank sample was confirmed near 641 mV vs RHE. It is considered that the change in the current density when the electrical potential was applied from positive to negative indicated the occurrence of an oxidation reaction of lactic acid. Further, it is presumed that the cause for the deactivation during the process was a decrease in the reaction rate due to poisoning of the catalyst surface. Moreover, the oxidation peak confirmed in the process of sweeping the electrical potential from positive to negative indicates that this reaction is an irreversible reaction. It is considered that the reason why the current value is higher than that in the first half is the occurrence of electron transfer due to dissociation of the material adsorbed onto the surface of the working electrode.

Figure 28:
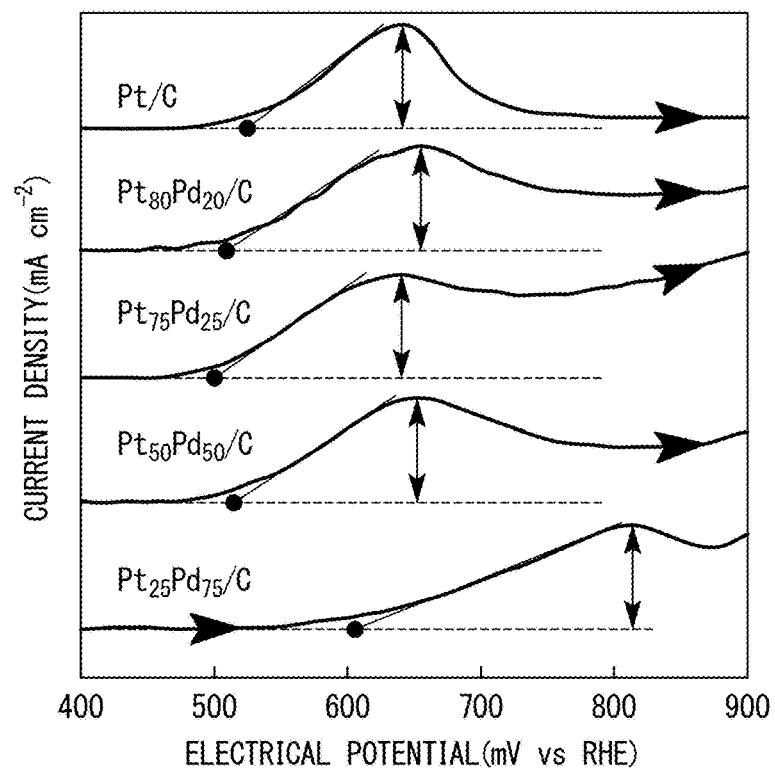
FIG. 28 is a diagram showing a result of the second cycle in a CV measurement in working electrodes containing the carbon-supported platinum-palladium alloy nanoparticle catalysts of Examples 1 to 6.

The results of the second cycle in the CV measurement in the working electrode containing the carbon-supported platinum-palladium alloy nanoparticle catalysts of Examples 1 to 6, which were standardized by the current density at the peak top generated when the electrical potential was swept from negative to positive, are shown in FIG. 28. Since the current density near 400 mV vs RHE was no different from the measurement result in the blank sample, the intersection between its extended line and the peak tangent was defined as the reaction onset potential. Table 7 shows the reaction onset potentials calculated therefrom.

TABLE 7

| | Catalyst composition | Reaction onset potential [mV vs RHE] |
|---|---|---|
| Production Example 5 | Pt/C | 527.2 |
| Production Example 2 | $Pt_{80}Pd_{20}/C$ | 507.5 |
| Production Example 1 | $Pt_{75}Pd_{25}/C$ | 498.8 |
| Production Example 3 | $Pt_{50}Pd_{50}/C$ | 512.6 |
| Production Example 4 | $Pt_{25}Pd_{75}/C$ | 605.4 |
| Production Example 6 | Pd/C | 814.2 |

From the results of Table 7, it was found that among the carbon-supported platinum-palladium alloy nanoparticle catalysts of Examples 1 to 6, the $Pt_{75}Pd_{25}/C$ catalyst exhibited the lowest reaction onset potential.

Controlled Potential Electrolysis (Chronoamperometry (CA)) Measurement

With respect to the Pt/C catalyst, $Pt_{80}Pd_{20}/C$ catalyst, $Pt_{75}Pd_{25}/C$ catalyst, and $Pt_{50}Pd_{50}/C$ catalyst whose reaction onset potentials are close to each other, the production distribution of pyruvic acid was investigated by CA at 650 mV vs RHE, which is near the electrical potential of the oxidation peak of the Pt/C catalyst, at 550 mV vs RHE, which is near the reaction onset potential of the Pt/C catalyst, and at 500 mV vs RHE, which is near the reaction onset potential of the $Pt_{75}Pd_{25}/C$ catalyst.

Figure 29:
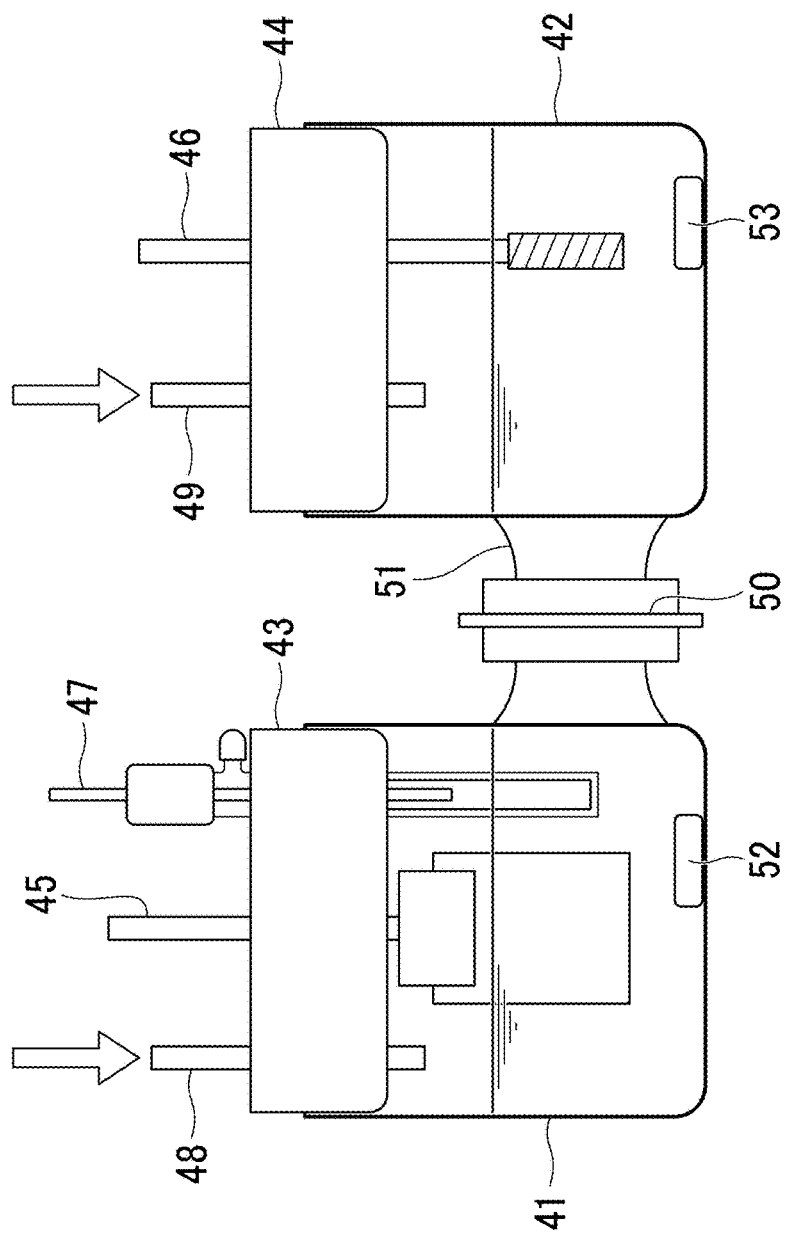
FIG. 29 is a schematic configuration diagram showing an electrochemical cell used for a CA measurement.

FIG. 29 is a schematic configuration diagram showing an electrochemical cell used for the CA measurement.

In FIG. 29, reference numeral 41 denotes a first cell, reference numeral 42 denotes a second cell, reference numeral 43 denotes a sealing plug that seals the first cell 41, reference numeral 44 denotes a sealing plug that seals the second cell 42, reference numeral 45 denotes a working electrode, reference numeral 46 denotes a counter electrode, reference numeral 47 denotes a reference electrode, reference numeral 48 denotes a first gas introduction pipe, reference numeral 49 denotes a second gas introduction pipe, reference numeral 50 denotes a diaphragm provided in the middle of a connecting portion 51 between the first cell 41 and the second cell 42, and reference numerals 52 and 53 denote stirring bars.

As the diaphragm 50, Nafion (registered trademark) NRE-212 manufactured by Sigma-Aldrich Co. LLC. was used.

As the working electrode 45, electrodes containing the carbon-supported platinum-palladium alloy nanoparticle catalysts of Examples 1 to 6 were installed. As the counter electrode 46, a platinum counter electrode (manufactured by BAS Inc.) having an electrode diameter of 0.5 mm and a length of 23 cm was used. As the reference electrode 47, an Ag/AgCl-saturated KCl silver-silver chloride reference electrode (manufactured by Inter Chemical Ltd.) was used.

As reaction solutions, 40 mL each of a 0.2 mol/L sodium sulfate aqueous solution containing 30 mmol/L lactic acid and a 0.2 mol/L sodium sulfate aqueous solution containing no substrate were introduced into the first cell 41 and the second cell 42, respectively.

Then, while bubbling an inert gas for 30 minutes, the reaction solutions in the first cell 41 and the second cell 42 were heated to 70° C. using hot stirrers equipped with the stirring bars 52 and 53, respectively, while stirring at 450 rpm.

After 30 minutes, it was confirmed that the liquid temperature reached 70° C., and the inert gas bubbling was switched to flowing.

Each electrode was connected to Versastat 4 manufactured by Princeton Applied Research, and the CV measurement was performed for 3 cycles at a scan rate of 10 mVs$^{-1}$ in the range of −100 mV vs RHE to +1,000 mV vs RHE.

Then, an electrical potential of 650 mV vs RHE, 550 mV vs RHE, or 500 mV vs RHE was applied and the reaction was performed at a constant potential for 2 hours, and the current density was plotted at intervals of 10 points/s.

Quantification of the product was performed by high performance liquid chromatography (HPLC) using a high performance liquid chromatograph Prominence manufactured by Shimadzu Corporation. A 50 mmol/L aqueous solution of perchloric acid was used as a buffer. 500 μL of the reaction solution was collected in a dedicated vial using a syringe, before the start of CA measurement, at the time when 1 hour had elapsed, and at the time of the completion of the reaction (at the time when 2 hours had elapsed), and the concentration of pyruvic acid was calculated from an area value of the measurement result of each reaction solution.

Figure 30:
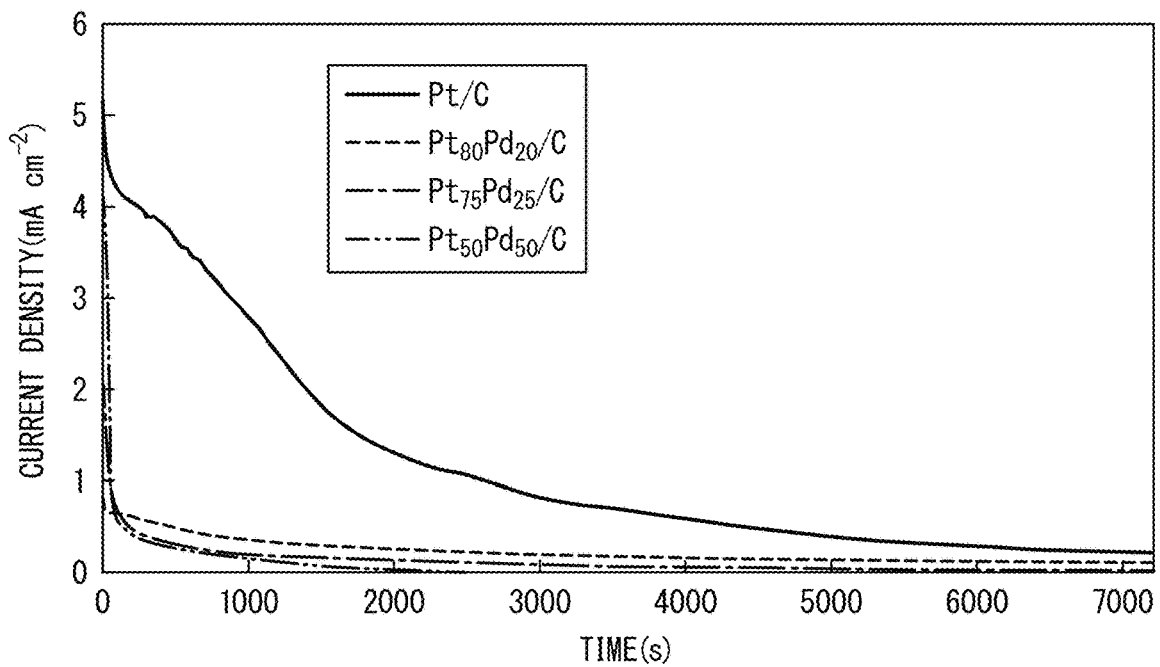
FIG. 30 is a diagram showing the time variation of the current density due to CA at each electrical potential in a $Pt_{80}Pd_{20}$/C catalyst, $Pt_{75}Pd_{25}$/C catalyst, and $Pt_{50}Pd_{50}$/C catalyst.
Figure 31:
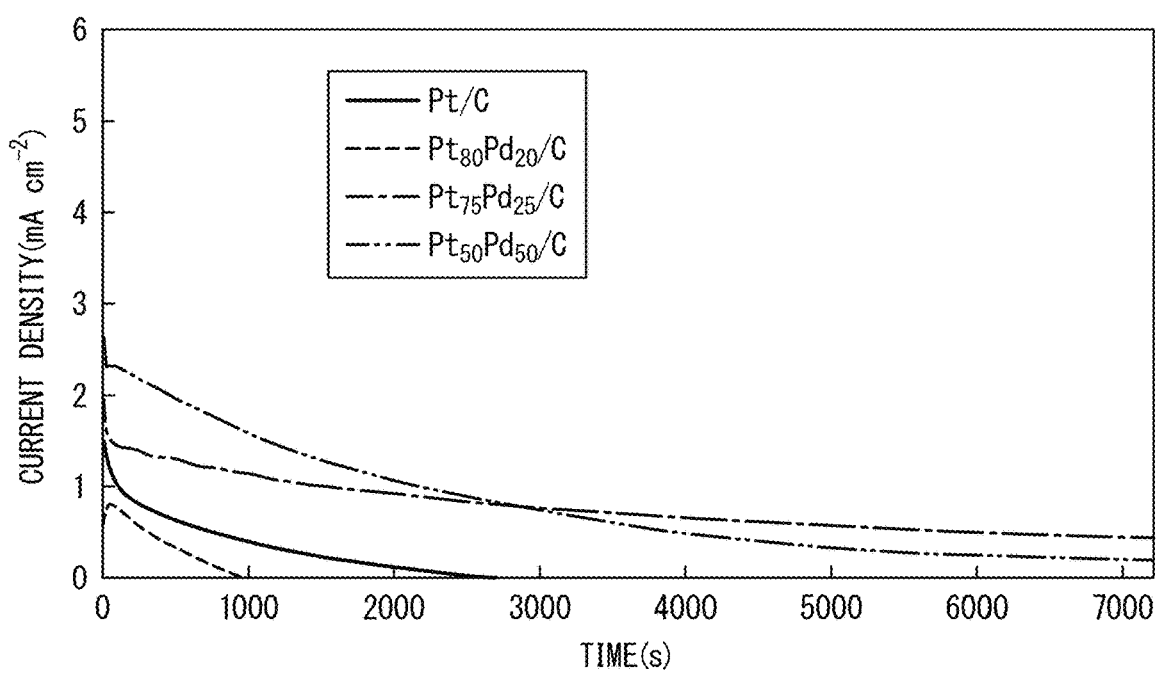
FIG. 31 is a diagram showing the time variation of the current density due to CA at each electrical potential in the $Pt_{80}Pd_{20}$/C catalyst, $Pt_{75}Pd_{25}$/C catalyst, and $Pt_{50}Pd_{50}$/C catalyst.
Figure 32:
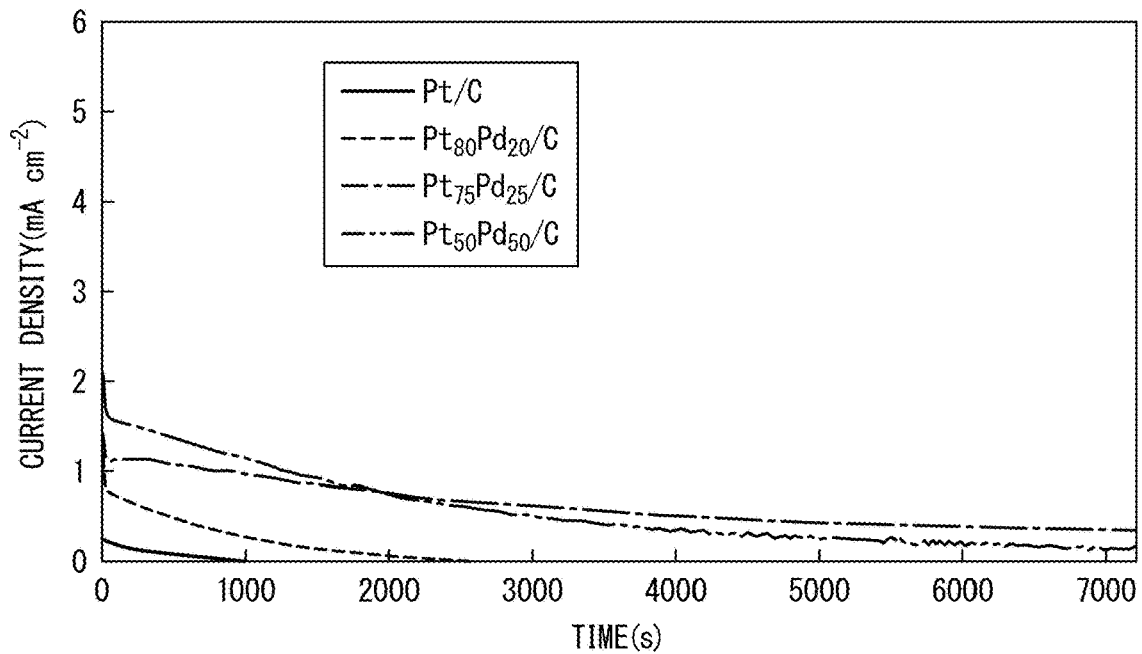
FIG. 32 is a diagram showing the time variation of the current density due to CA at each electrical potential in the $Pt_{80}Pd_{20}$/C catalyst, $Pt_{75}Pd_{25}$/C catalyst, and $Pt_{50}Pd_{50}$/C catalyst.

FIGS. 30 to 32 show the time variation of the current density due to CA at each electrical potential in the $Pt_{80}Pd_{20}/C$ catalyst, the $Pt_{75}Pd_{25}/C$ catalyst and the $Pt_{50}Pd_{50}/C$ catalyst. Further, Table 8 shows each electrical potential, the conversion rate of lactic acid in each carbon-supported platinum-palladium alloy nanoparticle catalyst, the production rate of pyruvic acid, and the Faradaic efficiency (F. E.) of pyruvic acid.

It should be noted that the conversion rate of lactic acid refers to the ratio of reacted lactic acid in the lactic acid introduced before the reaction, and was calculated by dividing the amount of lactic acid material after the completion of the reaction by the amount of lactic acid material before the start of CA measurement. The production rate of pyruvic acid refers to the ratio of pyruvic acid formed by the reaction from the lactic acid introduced before the reaction, and was calculated by dividing the amount of pyruvic acid material after the completion of the reaction by the amount of pyruvic acid material before the start of CA measurement. The Faradaic efficiency of pyruvic acid production refers to the ratio of the electric current used for the synthesis of pyruvic acid to the electric current flowing through the circuit, and was calculated by dividing, the total amount of electrons (mol) generated by the production of pyruvic acid generated which was calculated by multiplying the amount of pyruvic acid material produced and the number of electrons (2 electrons) generated along with the production of one molecule of pyruvic acid, by the total number of electrons (mol) flowing through the circuit which was calculated by dividing the total amount of electric charge flowing through the circuit by the Faraday constant (96490 (C/mol)).

TABLE 8

| Potential [mV vs RHE] | Conversion rate [%] | | | Pyruvic acid production rate [%] | | | F. E. [%] | | |
|---|---|---|---|---|---|---|---|---|---|
| | 650 | 550 | 500 | 650 | 550 | 500 | 650 | 550 | 500 |
| Pt/C | 19 | 0 | 0 | 24 | 0 | 0 | 114 | 0 | 0 |
| $Pt_{80}Pd_{20}$/C | 3 | 0 | 0 | 3 | 0 | 0 | 112 | 0 | 0 |
| $Pt_{75}Pd_{25}$/C | 7 | 10 | 11 | 2 | 11 | 12 | 112 | 100 | 110 |
| $Pt_{50}Pd_{50}$/C | 0 | 11 | 8 | 0 | 13 | 8 | 0 | 118 | 108 |

From the results of FIGS. 30 to 32 and Table 8, it was found that lactic acid was converted to pyruvic acid with a selectivity of 100% in the reaction on the working electrode containing the carbon-supported platinum-palladium alloy nanoparticle catalyst. It should be noted that the selectivity referred to here is the amount of pyruvic acid material produced with respect to the amount of the entire product material when performing HPLC on the solution at the time of the completion of the reaction. In the present experiment, among the products, since no product other than pyruvic acid was confirmed, the selectivity was 100%.

Although the final production rate of pyruvic acid by the working electrode containing the Pt/C catalyst was as high as 24% for 650 mV vs RHE, it was found that the production rate of pyruvic acid was lower, in the working electrodes containing other carbon-supported platinum-palladium alloy nanoparticle catalysts, than that of the working electrode containing the Pt/C catalyst. It is considered that this is because the measurement was made, for the working electrode containing the carbon-supported platinum-palladium alloy nanoparticle catalyst other than the Pt/C catalyst, after the oxidation peak potential, so that the surface of the working electrode was poisoned and the reaction rate decreased.

On the other hand, in the measurement at 500 mV vs RHE, which is lower than the reaction onset potential of the working electrode containing the Pt/C catalyst, the reaction did not proceed with the Pt/C catalyst, and the production rate of pyruvic acid with the $Pt_{75}Pd_{25}$/C catalyst whose reaction onset potential was the lowest was maximized.

From the above results, it became clear that it is possible to synthesize pyruvic acid from lactic acid with a selectivity of 100% even at a low electrical potential where the reaction does not proceed with the platinum catalyst, by using the working electrode containing the carbon-supported platinum-palladium alloy nanoparticle catalyst other than the Pt/C catalyst.

Figure 33:
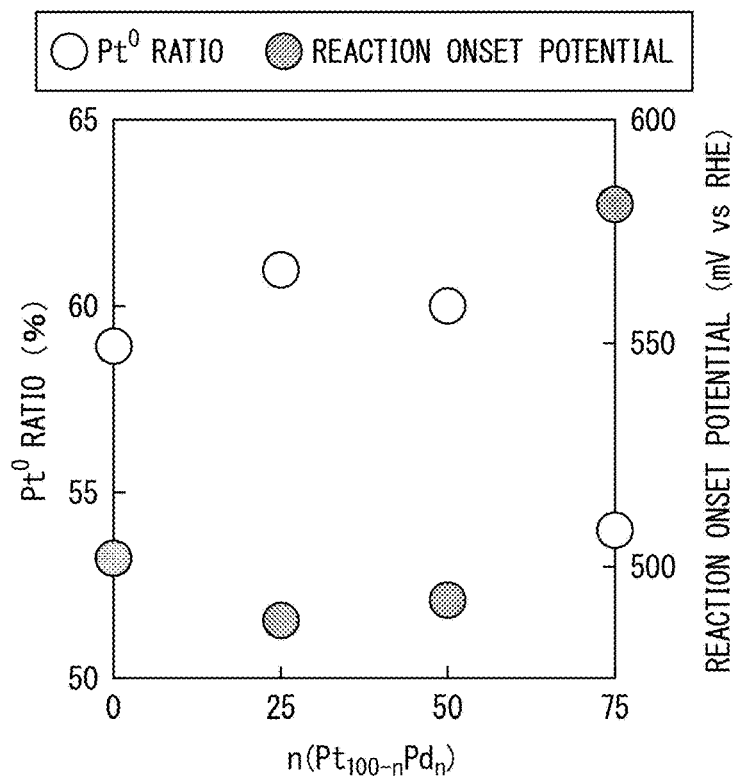
FIG. 33 is a diagram showing the calculated $Pt^0$ ratio and the reaction onset potential by analyzing the XPS measurement results of the carbon-supported platinum-palladium alloy nanoparticle catalyst represented by the general formula $Pt_{(100-n)}Pd_n$/C.

FIG. 33 shows the calculated $Pt^0$ ratio and the reaction onset potential by analyzing the XPS measurement result of the carbon-supported platinum palladium alloy nanoparticle catalyst represented by the general formula $Pt_{(100-n)}Pd_n$/C.

From the results of FIG. 33, it was found that the ratio of $Pt^0$ in the $Pt_{75}Pd_{25}$/C catalyst was the highest. It was also found that the $Pt_{75}Pd_{25}$/C catalyst had the lowest reaction onset potential.

Figure 34:
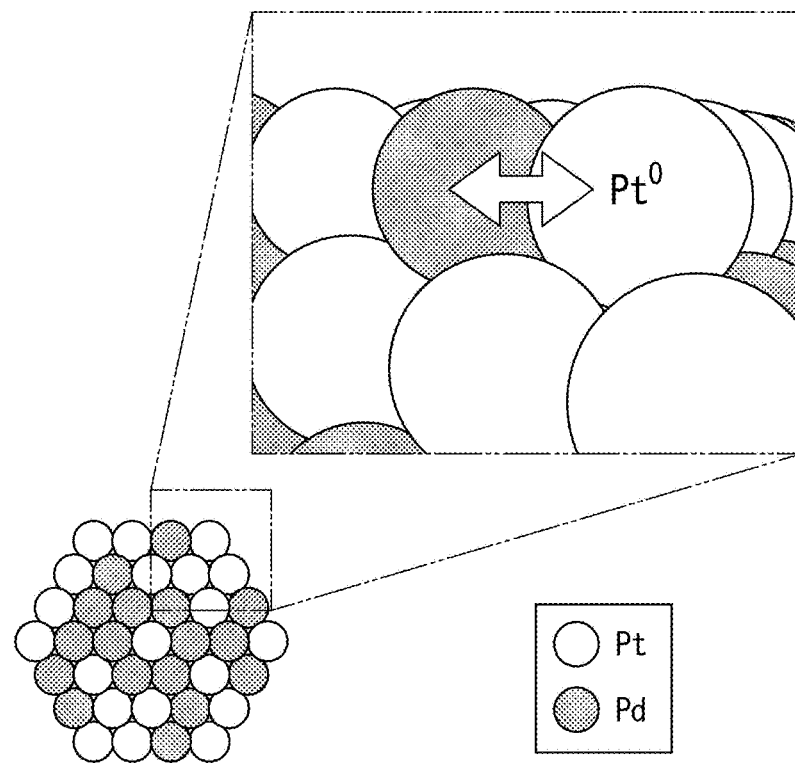
FIG. 34 is a schematic diagram showing a crystal structure of a carbon-supported platinum-palladium alloy nanoparticle catalyst represented by the general formula $Pt_{(100-n)}Pd_n$/C.

From the above results, it is considered that the cause for the high catalytic activity of the $Pt_{75}Pd_{25}$/C catalyst is, as shown in FIG. 34, the electronic interaction between Pt and Pd being stronger than those of the carbon-supported platinum-palladium alloy nanoparticle catalysts having other composition ratios, and thus the ratio of $Pt^0$ increased and the active sites increased.

REFERENCE SIGNS LIST

10: Fuel cell
11: Anode
12: Cathode
13: Electrolyte
20: Conducting wire
21: Voltmeter

What is claimed is:

1. A method for producing an α-keto acid,
the method comprising a step of using an alcohol as a raw material and using an electrode catalyst comprising an electrically conductive material carrying an alloy and having an electrical conductivity at 30° C. of $1\times10^{-13}$ $Scm^{-1}$ or more to carry out an electrochemical oxidation reaction of said alcohol,
wherein said alcohol is a secondary alcohol, and the secondary alcohol is a hydroxycarboxylic acid that is a substituent at an α-position of a carboxyl group, and
wherein said alloy comprises two or more transition metals.

2. A method for producing a pyruvic acid,
the method comprising a step of using an alcohol as a raw material and using an electrode catalyst comprising an electrically conductive material carrying an alloy and having an electrical conductivity at 30° C. of $1\times10^{-13}$ $Scm^{-1}$ or more to carry out an electrochemical oxidation reaction of said alcohol,
wherein said alcohol is a secondary alcohol, and the secondary alcohol is a hydroxycarboxylic acid that is a substituent at an α-position of a carboxyl group, and
wherein said alloy comprises two or more transition metals.

* * * * *